(12) United States Patent
Lally et al.

(10) Patent No.: US 11,833,044 B2
(45) Date of Patent: *Dec. 5, 2023

(54) DELIVERY SYSTEMS HAVING A TEMPORARY VALVE AND METHODS OF USE

(71) Applicant: Medtronic Vascular, Inc., Santa Rosa, CA (US)

(72) Inventors: Marian Lally, Galway (IE); James R. Keogh, Maplewood, MN (US); Jason Quill, Forest Lake, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 17/068,869

(22) Filed: Oct. 13, 2020

(65) Prior Publication Data

US 2021/0022860 A1 Jan. 28, 2021

Related U.S. Application Data

(63) Continuation of application No. 15/817,335, filed on Nov. 20, 2017, now Pat. No. 10,806,574.

(51) Int. Cl.
*A61F 2/24* (2006.01)
*A61B 17/12* (2006.01)
(Continued)

(52) U.S. Cl.
CPC ........ *A61F 2/2436* (2013.01); *A61B 17/1204* (2013.01); *A61B 17/12136* (2013.01);
(Continued)

(58) Field of Classification Search
CPC ...... A61F 2/2427; A61F 2/243; A61F 2/2433; A61F 2/2436; A61F 2/2439
See application file for complete search history.

(56) References Cited

U.S. PATENT DOCUMENTS 3,671,979 A * 6/1972 Moulopoulos ........ A61F 2/2427
623/2.11
4,056,854 A * 11/1977 Boretos ................. A61F 2/2436
623/2.18
(Continued)

FOREIGN PATENT DOCUMENTS

CN 102791223 A 11/2012

OTHER PUBLICATIONS

International Search Report and Written Opinion issued in International Application No. PCT/US2018/061876, dated Feb. 22, 2019.
(Continued)

*Primary Examiner* — Diane D Yabut
(74) *Attorney, Agent, or Firm* — Medler Ferro Woodhouse Mills PLLC

(57) ABSTRACT

A delivery system for percutaneously delivering a heart valve prosthesis to a site of a native heart valve includes a delivery catheter and a heart valve prosthesis. The delivery catheter includes an outer sheath, an inner shaft, and an orifice restriction mechanism. The heart valve prosthesis has a valve member and a docking member. When the orifice restriction mechanism is positioned within the docking member within an annulus of the native heart valve, the orifice restriction mechanism temporarily replicates the operation of the native heart valve until the valve member is positioned within the docking member.

16 Claims, 24 Drawing Sheets

(51) Int. Cl.
*A61M 60/295* (2021.01)
*A61M 60/894* (2021.01)
*A61M 60/497* (2021.01)
*A61M 60/174* (2021.01)

(52) U.S. Cl.
CPC .......... *A61F 2/2409* (2013.01); *A61F 2/2412* (2013.01); *A61F 2/2418* (2013.01); *A61F 2/2433* (2013.01); *A61M 60/174* (2021.01); *A61M 60/295* (2021.01); *A61M 60/497* (2021.01); *A61M 60/894* (2021.01); *A61F 2210/0014* (2013.01); *A61F 2230/0078* (2013.01); *A61F 2250/006* (2013.01); *A61F 2250/0059* (2013.01)

(56) References Cited

U.S. PATENT DOCUMENTS

| | | | |
|---|---|---|---|
| 6,146,396 A * | 11/2000 | Konya | A61B 17/221 606/159 |
| 6,425,916 B1 | 7/2002 | Garrison | |
| 7,621,948 B2 | 11/2009 | Herrmann et al. | |
| 8,105,375 B2 | 1/2012 | Navia et al. | |
| 8,591,460 B2 | 11/2013 | Wilson et al. | |
| 9,078,994 B2 | 7/2015 | Rosenman et al. | |
| 2004/0260394 A1 | 12/2004 | Douk et al. | |
| 2005/0010285 A1* | 1/2005 | Lambrecht | A61F 2/2412 623/2.18 |
| 2008/0077235 A1 | 3/2008 | Kirson | |
| 2009/0005863 A1 | 1/2009 | Goetz et al. | |
| 2009/0281609 A1 | 11/2009 | Benichou et al. | |
| 2011/0208297 A1 | 8/2011 | Tuval et al. | |
| 2012/0059458 A1 | 3/2012 | Buchbinder et al. | |
| 2013/0060328 A1 | 3/2013 | Rothstein | |
| 2013/0226290 A1 | 8/2013 | Yellin et al. | |
| 2013/0231735 A1 | 9/2013 | Deem et al. | |
| 2013/0310928 A1 | 11/2013 | Morriss et al. | |
| 2014/0039611 A1 | 2/2014 | Lane et al. | |
| 2014/0350669 A1 | 11/2014 | Gillespie et al. | |
| 2014/0379074 A1 | 12/2014 | Spence et al. | |
| 2015/0119981 A1 | 4/2015 | Khairkhahan et al. | |
| 2015/0238315 A1 | 8/2015 | Rabito et al. | |
| 2015/0297346 A1 | 10/2015 | Duffy et al. | |
| 2016/0361162 A1 | 12/2016 | Richter et al. | |

OTHER PUBLICATIONS

Office Action dated Feb. 28, 2023 in Chinese Appl. No. 201880073246.8.

* cited by examiner

DELIVERY SYSTEMS HAVING A TEMPORARY VALVE AND METHODS OF USE

CROSS-REFERENCE TO RELATED APPLICATIONS

This application is a continuation of U.S. application Ser. No. 15/817,335, filed Nov. 20, 2017, the contents of which are incorporated by reference herein in their entirety.

FIELD OF THE INVENTION

The present invention relates to systems for and methods of deploying a heart valve prosthesis at the site of a native heart valve. More particularly, the present invention relates to delivery systems for delivering a two-piece heart valve prosthesis within an annulus of a native heart valve.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream direction.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate. Valvular stenosis may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered, positioned and deployed at the site of the diseased heart valve through catheter-based delivery systems. Heart valve prostheses can be delivered while in a low-profile or radially collapsed configuration so that the heart valve prosthesis can be advanced through the patient's vasculature. Once positioned at the treatment site, the heart valve prosthesis can be expanded to engage tissue at the diseased heart valve region to, for instance, hold the heart valve prosthesis in position. However, challenges exist with reducing the crossing profile of heart valve prostheses for use in, for example, transseptal approaches to a native mitral valve.

To address the crossing profile concern, the heart valve prosthesis may be split into two separate components. Splitting the heart valve prosthesis into two separate components allows each component to be collapsed separately to a reduced crossing profile. However, splitting the heart valve prosthesis into two separate components presents challenges to the successful repair and replacement of the native heart valve. In particular, leaflet function of the native valve is impaired as the two-piece valve is deployed. Accordingly, there is a need for delivery systems and methods that provide a mechanism to act as a temporarily heart valve during delivery and positioning of a two-piece heart valve prosthesis.

BRIEF SUMMARY OF THE INVENTION

Embodiments hereof relate to a delivery system for percutaneously delivering a heart valve prosthesis to a site of a native heart valve. The delivery system includes a delivery catheter and a heart valve prosthesis. The delivery catheter includes an outer sheath, an inner shaft, and an orifice restriction mechanism. In some embodiments, the orifice restriction mechanism is a pulsatile balloon. The inner shaft is slidably disposed within the outer sheath. The orifice restriction mechanism is coupled to a distal portion of the inner shaft. In some embodiments, wherein the orifice restriction mechanism is a pulsatile balloon, the pulsatile balloon has a first state and an inflated second state. The heart valve prosthesis includes a valve member and a docking member. The valve member and the docking member each have a radially collapsed configuration and a radially expanded configuration. The orifice restriction mechanism is configured to be positioned within the docking member after the docking member is in the radially expanded configuration within an annulus of the native heart valve. The orifice restriction mechanism is further configured to temporarily replicate the operation of the native heart valve when positioned within the docking member in the radially expanded configuration within the annulus of the native heart valve until the valve member is positioned within the docking member.

Embodiments hereof further relate to a delivery system for percutaneously delivering a heart valve prosthesis to a site of a native heart valve. The delivery system includes a heart valve prosthesis and a delivery catheter assembly comprising one or more catheters and one or more sheath assemblies. The heart valve prosthesis includes a valve member and a docking member, each having a radially collapsed configuration and a radially expanded configuration. The delivery catheter system includes an inner shaft assembly, a docking sheath assembly, and a valve sheath assembly. The inner shaft assembly has an inner shaft and an orifice restriction mechanism. In some embodiments, the delivery catheter system includes a single catheter comprising the docking sheath assembly and the valve sheath assembly. In some embodiments, the delivery catheter system includes two catheters wherein a first catheter comprises the docking sheath assembly and a second catheter comprises the valve sheath assembly. In some embodiments, the docking sheath assembly and the valve sheath assembly are the same sheath assembly. In some embodiments, the docking sheath assembly and the valve sheath assembly are different sheath assemblies. The docking sheath assembly has an inner sheath and an outer sheath. The inner sheath of the docking sheath assembly is configured to slidably receive the inner shaft assembly. The outer sheath of the docking sheath assembly is configured to slidably receive the inner sheath and is further configured to retain the docking member of the heart valve prosthesis in the radially collapsed configuration for delivery to a desired treatment location. The valve sheath assembly has an inner sheath and an outer sheath. The inner sheath of the valve sheath assembly is configured to slidably receive the inner shaft assembly. The outer sheath of the valve sheath assembly is configured to slidably receive the inner sheath. The outer sheath of the valve sheath assembly is further configured to retain the valve member of the heart valve prosthesis in the radially collapsed configuration for delivery to a desired treatment location. The orifice restriction mechanism is coupled to a distal portion of the inner shaft. The orifice restriction mechanism has a first state and a second state. The orifice restriction mechanism is configured to be positioned within the docking member of the heart valve prosthesis in the radially expanded configuration at an annulus of the native heart valve. The orifice restriction mechanism is further configured to restrict blood flow through the native heart valve when in the second state and positioned within the docking member of the heart valve prosthesis in the radially expanded configuration at the annulus of the native heart valve. In some embodiments, the orifice restriction mechanism is a pulsatile balloon mechanism.

Embodiments hereof also relate to a method of delivering and positioning a heart valve prosthesis at a site of a native heart valve. A delivery catheter assembly includes an inner shaft, an outer sheath, and an orifice restriction mechanism, e.g., a pulsatile balloon. In some embodiments, a delivery catheter with a heart valve prosthesis including a docking member and a valve member each retained in a radially collapsed configuration is advanced to a native valve of a heart. The docking member of the heart valve prosthesis is positioned within an annulus of the native heart valve. The outer sheath of the delivery catheter is retracted to release the orifice restriction mechanism, e.g., a pulsatile balloon, and the docking member. The docking member is expanded to the radially expanded configuration. The orifice restriction mechanism is positioned within the docking member at the annulus of the native heart valve. In some embodiments, wherein the orifice restriction mechanism is a pulsatile balloon, the pulsatile balloon is cyclically transitioned between a first state and an inflated second state. The cyclic transitions are synchronized with the cardiac cycle of the heart. When the clinician is ready to position the valve member within the docking member, the pulsatile balloon is transitioned to the first state. The delivery catheter is advanced to position the valve member of the heart valve prosthesis within the docking member at the annulus of the native heart valve. The outer sheath is retracted to release the valve member of the heart valve prosthesis. The valve member expands to a radially expanded configuration.

Embodiments hereof also relate to a method of delivering and positioning a heart valve prosthesis at a site of a native heart valve. A delivery system with a docking member of a heart valve prosthesis in a radially collapsed configuration is advanced through a native heart valve and into an adjacent chamber of a heart. The delivery system includes an inner shaft inner shaft assembly and a docking sheath assembly. The inner shaft assembly has an inner shaft and an orifice restriction mechanism in a first state. The docking sheath assembly has an outer sheath and an inner sheath. The outer sheath is configured to slidably receive the inner sheath, and the inner sheath is configured to slidably receive the inner shaft. The docking sheath assembly further includes the docking member of the heart valve prosthesis in a radially collapsed configuration at a distal portion thereof. The docking sheath assembly is retracted to release the orifice restriction mechanism. The docking sheath assembly is manipulated to position the docking member of the heart valve prosthesis within an annulus of the native heart valve. The outer sheath of the docking sheath assembly is retracted to release the docking member. The docking member expands to a radially expanded configuration. The delivery system is retracted to position the orifice restriction mechanism within the docking member at the annulus of the native heart valve. The orifice restriction mechanism is transitioned from the first state to a second state. The docking sheath assembly is exchanged for a valve sheath assembly. The valve sheath assembly has an outer sheath and an inner sheath slidingly disposed over the inner shaft. The valve sheath assembly further includes a valve member of the heart valve prosthesis in a radially collapsed configuration at a distal portion thereof. The valve member of the heart valve prosthesis is positioned adjacent the native heart valve. When the clinician is ready to position the valve member within the docking member, the delivery system is advanced to position the valve member of the heart valve prosthesis within the docking member at the annulus of the native heart valve. The outer sheath of the valve sheath assembly is retracted to release the valve member. The valve member expands to a radially expanded configuration within the docking member. The orifice restriction mechanism is transitioned from the second state to the first state.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician.

The following detailed description is merely exemplary in nature and is not intended to limit the invention or the application and uses of the invention. Although the description of embodiments hereof is in the context of delivery systems for delivering a heart valve prosthesis within a native mitral valve, the delivery systems described herein can also be used in other valves of the body, or for delivering a heart valve prosthesis within a failed previously implanted heart valve prosthesis. Furthermore, there is no intention to be bound by any expressed or implied theory presented in the preceding technical field, background, brief summary or the following detailed description.

Figure 1:
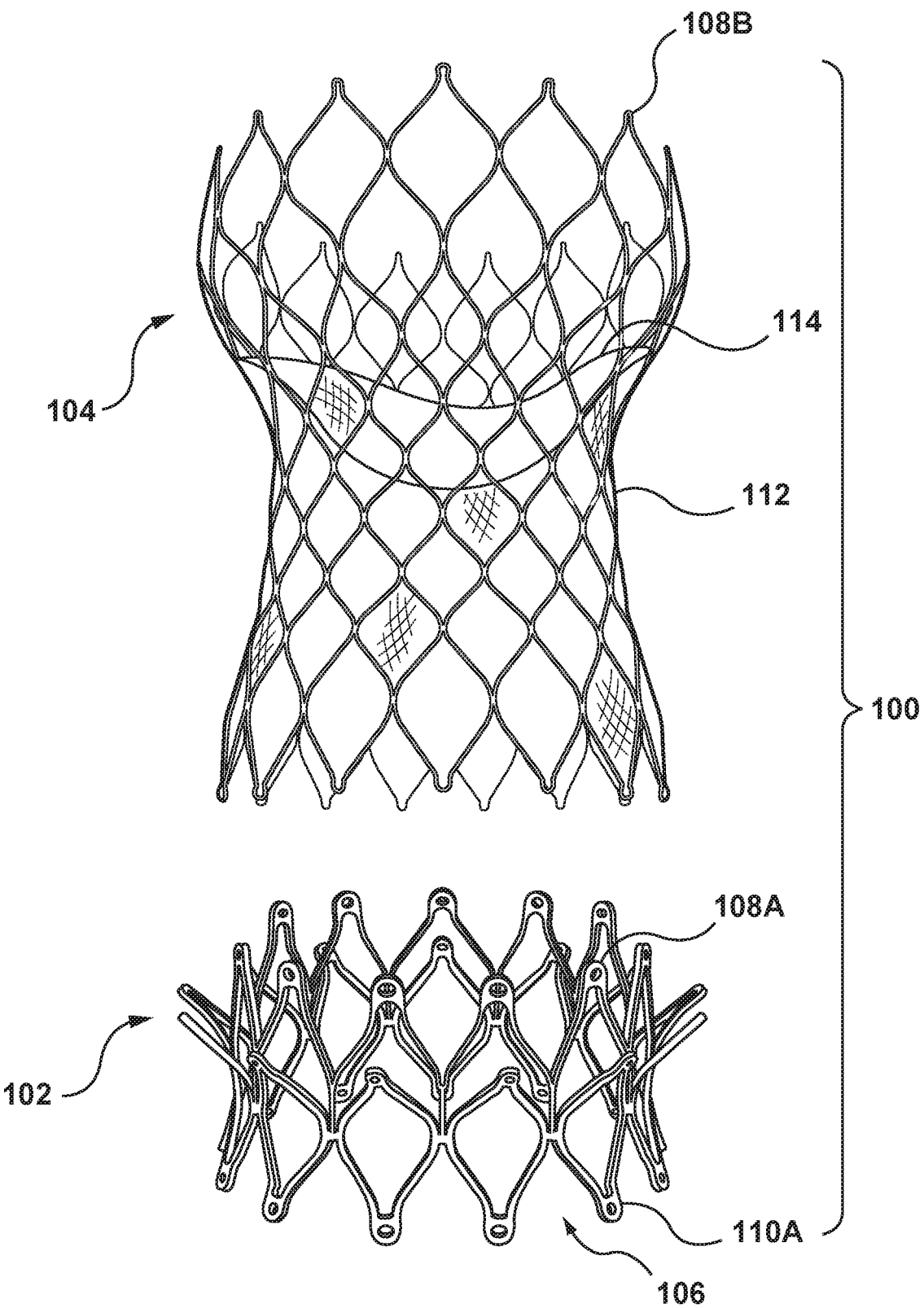
FIG. 1 is a perspective view illustration of a two-piece heart valve prosthesis having a docking member and a valve member, wherein the docking member and the valve member are each in their radially expanded configurations.

The present invention in various embodiments relate to a delivery system for delivering, positioning and deploying a two-piece heart valve prosthesis at a site of a native heart valve. FIG. 1 is a perspective view of an exemplary two-piece heart valve prosthesis 100 for use in embodiments hereof, wherein the heart valve prosthesis 100 is in a radially expanded configuration. The heart valve prosthesis 100 is illustrated herein in order to facilitate description of delivery catheters and systems to be utilized in conjunction therewith according to embodiments hereof. While the heart valve prosthesis 100 illustrated herein is of a specific construction and structure, it is not meant to be limiting, and alternate heart valve prostheses can be used with the methods and devices described herein. The heart valve prosthesis 100 is merely exemplary. It is understood that any number of alternate heart valve prostheses can be used with the methods and devices described herein. Further, while described herein as a heart valve prosthesis, this is done as an example for convenience, and the heart valve prosthesis may assume various configurations for use at other locations within the heart and the body.

In the embodiment of FIG. 1, the heart valve prosthesis 100 includes a docking member 102, also referred to herein as an anchoring member or anchor stent, and a valve member 104, also referred to herein as a valve stent in accordance with an embodiment hereof. The docking member 102 and the valve member 104 are each shown in a radially expanded configuration in FIG. 1. The docking member 102 is configured to be positioned and expanded to the radially expanded configuration at an annulus of a native heart valve. After deployment of the docking member 102, the valve member 104 is configured to be positioned within the radially expanded docking member 102 and expanded to a radially expanded configuration. The docking member 102 and the valve member 104 combine to replicate the operation of the native heart valve.

The docking member 102, as shown in FIG. 1, is a stent or frame, which can have, for example, a flared, funnel-like or hyperboloid shape. Accordingly, the docking member 102 defines a lumen 106 extending from an inflow end 108A to an outflow end 110A thereof. The docking member 102 includes the radially collapsed configuration for delivery and the radially expanded configuration when deployed. The docking member 102 is configured to engage tissue at the annulus of the native heart valve when in the radially expanded configuration. The docking member 102 is further configured to provide a secure mounting surface with which the valve member 104 may engage, when the valve member 104 is in the radially expanded configuration within the lumen 106 of the docking member 102. Embodiments of the docking member 102 may include structural components such as, but not limited to a plurality of struts or wire portions arranged relative to each other to provide a desired compressibility and strength. As described herein, the docking member 102 is self-expanding from the radially collapsed configuration to the radially expanded configuration. "Self-expanding" as used herein means that a structure has been formed or processed to have a mechanical or shape memory to return to the radially expanded configuration. Mechanical or shape memory may be imparted to the structure using techniques understood in the art. Alternatively, the docking member 102 may be balloon expandable or mechanically expandable. The docking member 102 may be made from materials such as, but not limited to stainless steel, nickel-titanium alloys (e.g. NITINOL), or other suitable materials.

Also shown in FIG. 1, the valve member 104 of the heart valve prosthesis 100 includes a generally cylindrical frame or valve support 112 and a prosthetic valve 114 coupled to, mounted within, or otherwise carried by the valve support 112. The valve member 104 is configured for placement within the lumen 106 of the docking member 102 such that the heart valve prosthesis 100 replicates the function of the native heart valve when deployed at the annulus of the native heart valve. The valve member 104 includes a radially collapsed configuration for delivery and the radially expanded configuration when deployed. Embodiments of the valve support 112 may include various structural components such as, but not limited to a plurality of struts or wire portions arranged relative to each other to provide a desired compressibility and strength. While the valve support 112 is described herein as self-expanding from the radially collapsed configuration to the radially expanded configuration, this is not meant to limit the design, and in other embodiments, the valve support 112 may be balloon expandable or mechanically expandable. The valve support 112 may be made from materials such as, but not limited to stainless steel, nickel-titanium alloys (e.g. NITINOL), or other suitable materials.

As previously described, the heart valve prosthesis 100 includes the prosthetic valve 114 within the interior of the valve member 104. In an embodiment hereof, the prosthetic valve 114 is positioned adjacent to the inflow end 108B of the valve member 104. The prosthetic valve 114 is configured as a one-way valve to allow blood flow in one direction and thereby regulate blood flow therethrough. The prosthetic valve 114 is capable of blocking flow in one direction to regulate flow therethrough via valve leaflets that may form a bicuspid or tricuspid replacement valve. More particularly, if the heart valve prosthesis 100 is configured for placement within a native heart valve having two leaflets such as the mitral valve, the prosthetic valve 114 may include two valve leaflets to form a bicuspid replacement valve that closes with pressure on the outflow and opens with pressure on the inflow. In other embodiments in accordance herewith, the prosthetic valve 114 may be a tricuspid replacement valve or may be a single leaflet replacement valve. The valve leaflets are sutured or otherwise securely and sealingly attached to an inner circumference of the valve member 104.

The valve leaflets of prosthetic valve 114 may be made of natural pericardial material obtained from, for example, heart valves, aortic roots, aortic walls, aortic leaflets, pericardial tissue, bypass grafts, blood vessels, intestinal submucosal tissue, umbilical tissue and the like from humans or animals, such as tissue from bovine, equine or porcine origins. Alternatively, the valve leaflets of prosthetic valve 114 may be made of synthetic materials suitable for use as heart valve prosthesis leaflets in embodiments hereof including, but are not limited to polyester, polyurethane, cloth materials, nylon blends, and polymeric materials.

Embodiments hereof relate to delivery catheters or devices for percutaneously delivering a two-piece heart valve prosthesis (e.g., the heart valve prosthesis 100 described above) to a native heart valve. As will be described in more detail herein, the delivery catheter includes an orifice restriction mechanism, e.g., a temporary valve, that is configured to temporarily mimic or replicate the operation of the native heart valve during deployment of the two-piece heart valve prosthesis. More specifically, after the docking member 102 of the heart valve prosthesis 100 is deployed within the annulus of a native heart valve, the orifice restriction mechanism or temporary valve according to embodiments hereof is configured to temporarily replace the function of the native heart valve until the valve member 104 of the heart valve prosthesis 100 is deployed within the docking member 102.

Figure 2:
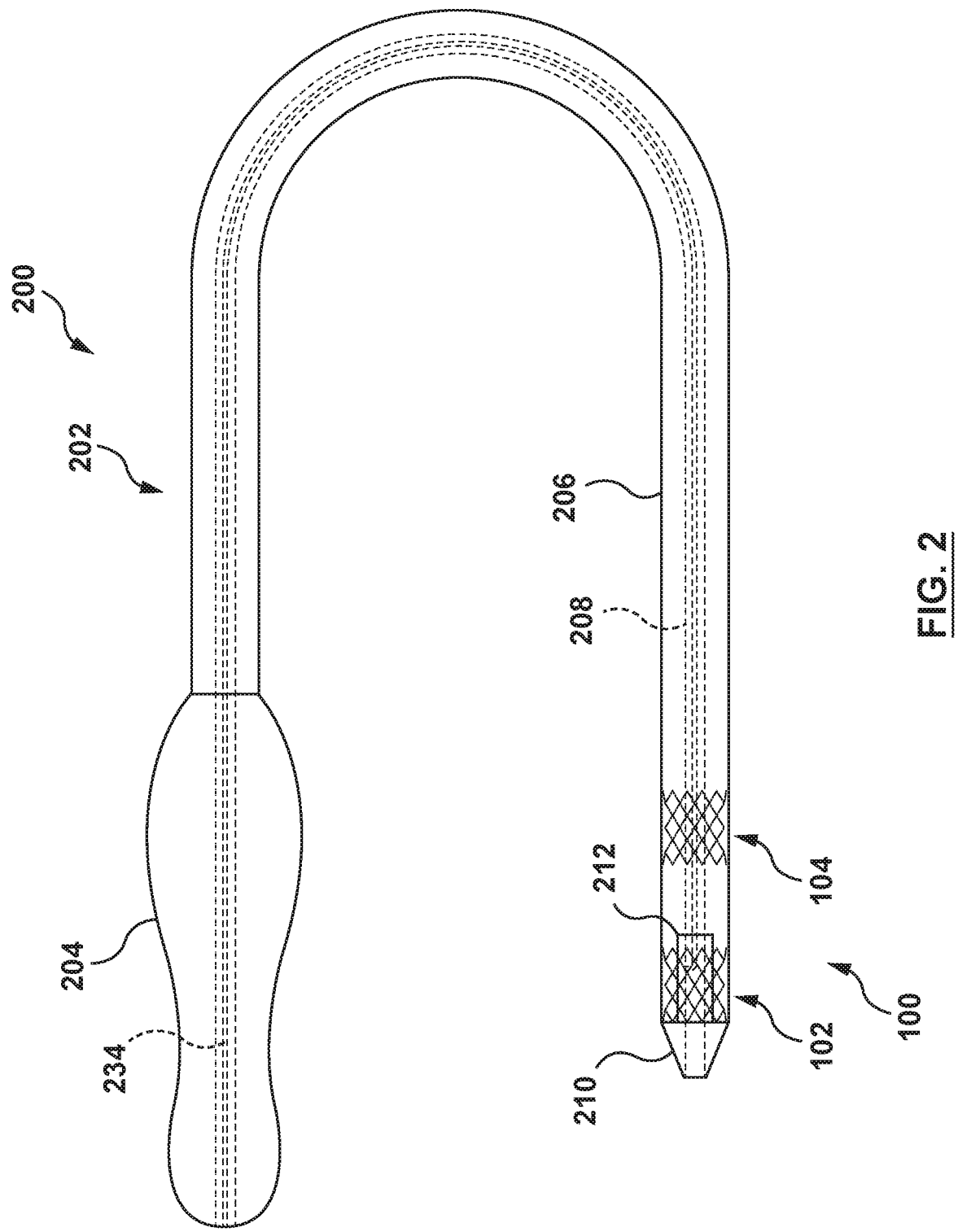
FIG. 2 is a side view illustration of a delivery system configured in accordance with an embodiment hereof, wherein the docking member and the valve member of the heart valve prosthesis of FIG. 1 are mounted at a distal portion thereof, the docking member and the valve member each being shown in their radially collapsed configurations for delivery, wherein the delivery system includes an orifice restriction mechanism in a delivery state.
Figure 2A:
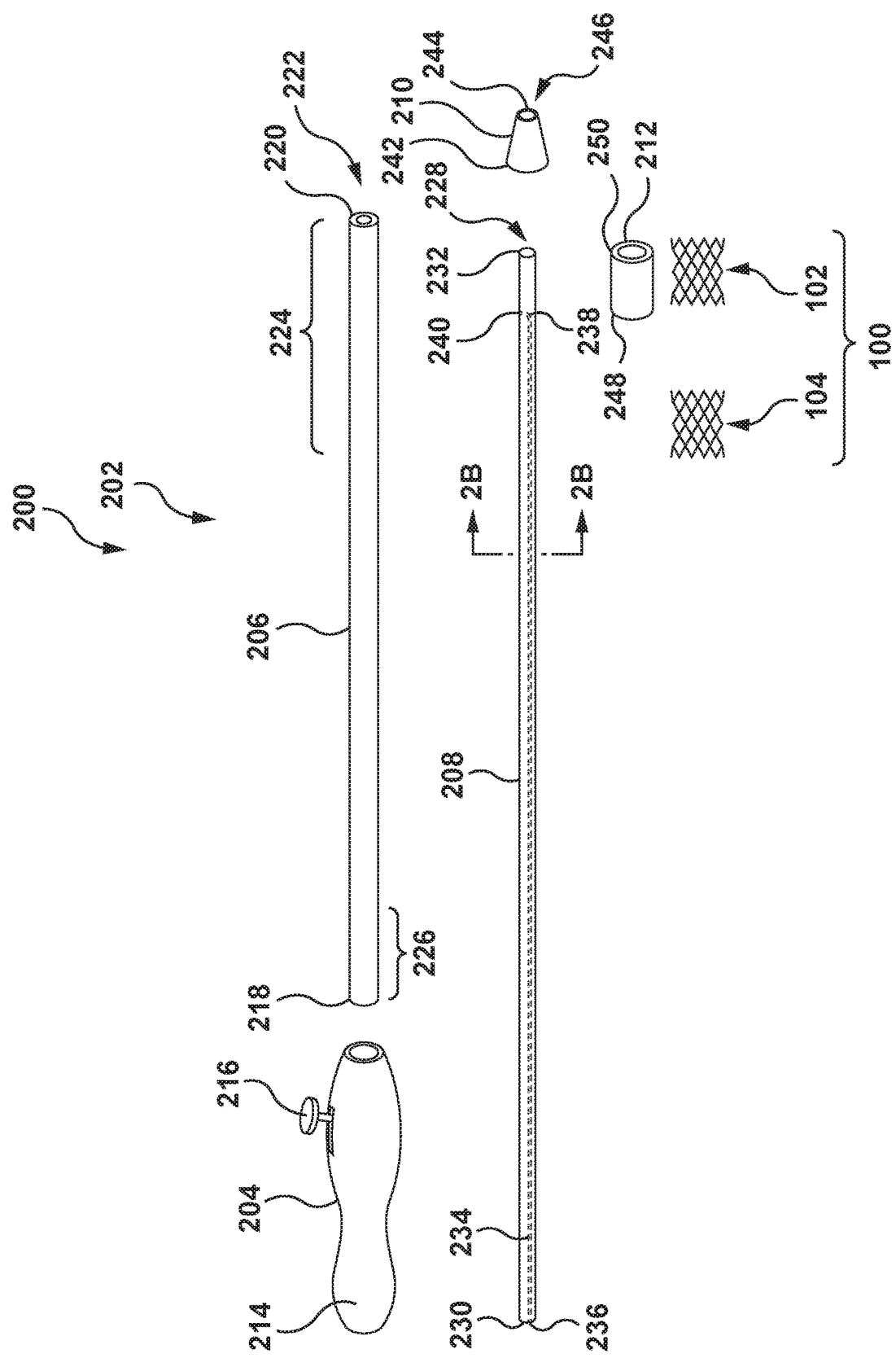
FIG. 2A is an exploded perspective view illustration of the delivery system of FIG. 2.
Figure 2B:
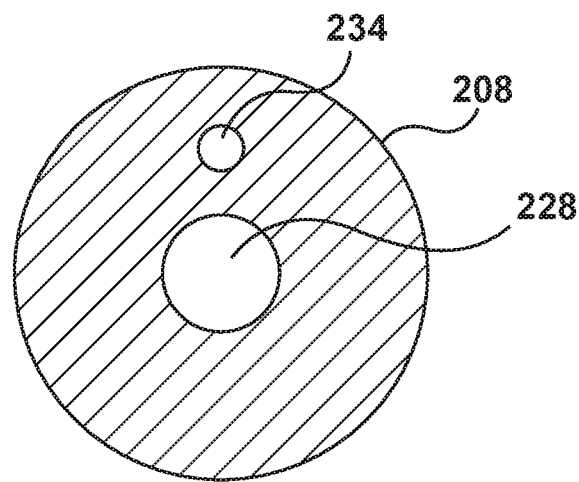
FIG. 2B is a cross-sectional view illustration of an inner shaft of the delivery system of FIG. 2, taken at line 2B-2B of FIG. 2A.
Figure 2C:
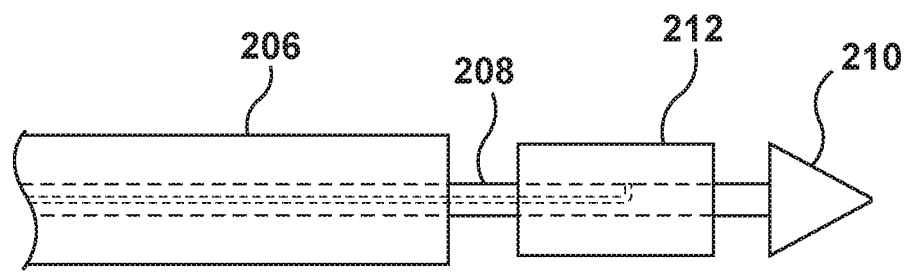
FIG. 2C is a side view illustration of a distal portion of the delivery system of FIG. 2, wherein the orifice restriction mechanism is in a first state.
Figure 2D:
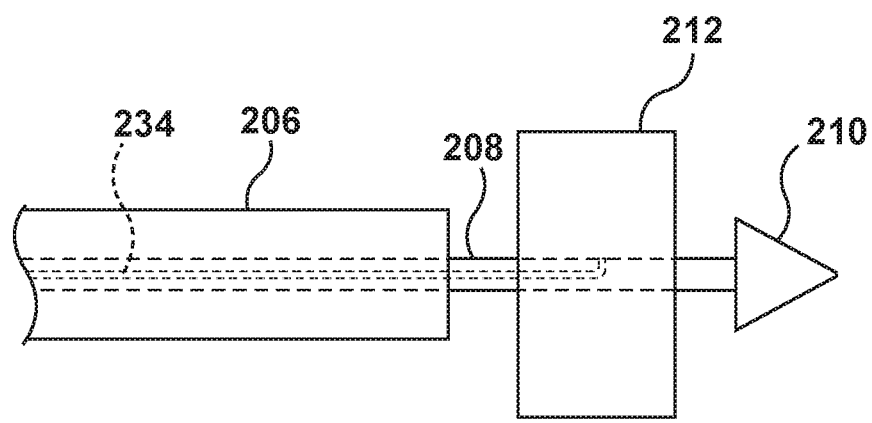
FIG. 2D is a side view illustration of the distal portion of the delivery system of FIG. 2, wherein the orifice restriction mechanism is in an inflated second state.

FIGS. 2-2D illustrate a delivery system 200 according to an embodiment hereof in which the orifice restriction mechanism is a pulsatile balloon 212 that is configured to inflate and deflate in synchronization with the cardiac cycle of the heart. As shown in FIG. 2, the delivery system 200 includes a delivery catheter 202 and the heart valve prosthesis 100 previously described herein. The delivery catheter 202 includes a handle 204, an outer sheath 206, an inner shaft 208, a distal tip 210, and a pulsatile balloon 212. In this embodiment, the separate components of the heart valve prosthesis 100, i.e., the docking member 102 and the valve member 104, are spaced axially on a distal portion of the delivery catheter 202. The docking member 102 is mounted distal to the valve member 104, with each of the valve member 104 and the docking member 102 in a radially collapsed configuration for delivery to a desired treatment location. The delivery system 200 is configured to deliver and implant the heart valve prosthesis 100 according to an embodiment of the present invention.

As best shown in FIG. 2A, the handle 204 includes a housing 214 and an actuation mechanism 216 for interfacing by a user. The handle 204 provides a surface for convenient handling and grasping by a user, and while the handle 204 of FIGS. 2-2A is shown with a generally cylindrical shape, this is by way of example and not limitation, and other shapes and sizes may be utilized. Further, while the handle 204 is shown with a specific style of actuation mechanism 216, this is also by way of example and not limitation, and various actuation mechanisms may be utilized including, but not limited to an axially-slidable lever, a rotary rack and pinion gear, or other applicable actuation mechanisms.

Also shown in FIG. 2A, the outer sheath 206 includes a proximal end 218, a distal end 220, and a lumen 222 extending from the proximal end 218 to the distal end 220 of the outer sheath 206. The lumen 222 of the outer sheath 206 is sized to receive the inner shaft 208. A distal portion 224 of the outer sheath 206 is configured to retain the valve member 104 and the docking member 102 of the heart valve prosthesis 100 in their radially collapsed configurations for delivery to the desired treatment location. The distal portion 224 is further configured to encapsulate or cover the pulsatile balloon 212 in a first state, also referred to as the uninflated state, therein for delivery to the desired treatment site. While the distal portion 224 is described herein as a distal portion of the outer sheath 206, in an embodiment, the distal portion 224 may be a separate component, such as a capsule, coupled to the distal end 220 of the outer sheath 206. Moreover, although the outer sheath 206 is described herein as a single component, this is by way of example and not limitation, and the outer sheath 206 may include multiple components such as, but not limited to proximal and distal shafts or other components suitable for the purposes described herein. In an embodiment, the proximal end 218 of the outer sheath 206 is configured for fixed connection to the handle 204. More specifically, the proximal end 218 may extend proximally into the housing 214 of the handle 204 and a proximal portion 226 of the outer sheath 206 may be operably coupled to the actuation mechanism 216 of the handle 204. The proximal portion 226 is operably coupled to the actuation mechanism 216 such that movement of the actuation mechanism 216 causes the outer sheath 206 and the distal portion 224 to move relative to the inner shaft 208. The outer sheath 206 is thus movable relative to the handle 204 and the inner shaft 208 by the actuation mechanism 216. However, if the actuation mechanism 216 is not moved and the handle 204 is moved, the outer sheath 206 moves with the handle 204, not relative to the handle 204. The outer sheath 206 may be constructed of materials such as, but not limited to polyurethane (e.g. Pellethane®, Elasthane™, Texin®, Tecothane®), polyamide polyether block copolymer (e.g. Pebax®, nylon 12), polyethylene, or other materials suitable for the purposes of the present disclosure. The proximal portion 226 of the outer sheath 206 may be operably coupled to the actuation mechanism 216, for example, and not by way of limitation by adhesives, bonding, welding, fusing, mechanical connection, or other coupling devices as appropriate.

The inner shaft 208 of the delivery catheter 202 extends within the lumen 222 of the outer sheath 206, as shown in FIG. 2A. The inner shaft 208 includes a lumen 228 extending from a proximal end 230 to a distal end 232 of the inner shaft 208. The lumen 228 is sized to receive auxiliary components, such as a guidewire. At least a portion of the inner shaft 208 is configured for fixed connection to the handle 204. In an embodiment, the proximal end 230 of the inner shaft 208 may extend through the housing 214 and be coupled to the handle 204. During sliding or longitudinal movement of the outer sheath 206 relative thereto, the inner shaft 208 is fixed relative to the handle 204. Although the inner shaft 208 is described herein as a single component, this is by way of example and not limitation, and the inner shaft 208 may include multiple components such as, but not limited to proximal and distal shafts or other components suitable for the purposes described herein. The inner shaft 208 may be formed of materials such as but not limited to polyurethane (e.g. Pellethane©, Elasthane™, Texin®, Tecothane®), polyamide polyether block copolymer (e.g. Pebax®, nylon 12), polyethylene, or other materials suitable for the purposes described herein. The inner shaft 208 may be coupled to the handle 204 by adhesives, bonding, welding, fusing, mechanical connection, or other coupling methods as appropriate.

The inner shaft 208 further includes an inflation lumen 234, as shown in FIGS. 2-2B. The inflation lumen 234 is defined within a wall of the inner shaft 208, as best shown in the cross-sectional view of the inner shaft 208 of FIG. 2B. The inflation lumen 234 includes a proximal end 236 and a distal end 238 in fluid communication with an inflation port 240, as shown in FIG. 2A. The inflation port 240 is in fluid communication with an interior of the pulsatile balloon 212.

The distal tip 210 is coupled to the distal end 232 of the inner shaft 208. With additional reference to FIG. 2A, the distal tip 210 includes a proximal end 242, a distal end 244, and a lumen 246 extending from the proximal end 242 to the distal end 244 of the distal tip 210. The lumen 246 is sized to receive auxiliary components, such as a guidewire. The proximal end 242 of the distal tip 210 is coupled to the distal end 232 of the inner shaft 208 such that the lumen 246 of the distal tip 210 is longitudinally aligned and in fluid communication with the lumen 228 of the inner shaft 208. Thus, the inner shaft 208 with the distal tip 210 coupled thereto form a continuous lumen from the proximal end 230 of the inner shaft to the distal end 244 of the distal tip. The distal tip 210 may be coupled to the inner shaft 208 by methods such as, but not limited to adhesives, bonding, welding, fusing, mechanical connection, or other coupling methods as appropriate.

The pulsatile balloon 212 is mounted over a distal portion of the inner shaft 208. More particularly, as shown in FIG. 2A, the pulsatile balloon 212 includes a proximal end 248 coupled to the inner shaft 208 and a distal end 250 coupled to the inner shaft 208. The pulsatile balloon 212 includes the uninflated or first state wherein the pulsatile balloon 212 is not inflated, as shown in FIG. 2C, which is a side view of a distal portion of the delivery catheter 202 with the outer sheath 206 proximally retracted. For sake of clarity, the docking member 102 of the heart valve prosthesis 100 is omitted in FIG. 2C. Stated another way, the outer sheath 206 has been proximally retracted and the docking member 102 of the heart valve prosthesis 100 has been omitted from the illustration to clearly show the pulsatile balloon 212 in the uninflated state. When the docking member 102 is not omitted and the outer sheath 206 is not retracted for clarity, the docking member 102 in the radially collapsed configuration would be disposed about the pulsatile balloon 212 in the uninflated state and the pulsatile balloon 212 and the docking member 102 would be received within the outer sheath 206.

The pulsatile balloon 212 further includes the inflated second state, wherein the pulsatile balloon 212 is inflated via inflation fluid delivered under pressure through the inflation lumen 234 to the interior of the pulsatile balloon 212, as shown in FIG. 2D. In FIG. 2D, the outer sheath 206 has been proximally retracted, the docking member 102 of the heart valve prosthesis 100 has been released and radially expanded to the radially expanded state and for ease of illustration, has thus been omitted, and the pulsatile balloon 212 is in the inflated second state. The pulsatile balloon 212 is configured to transition from the uninflated state to the inflated second state and back in a repetitive cycle synchronized to the cardiac cycle of the heart such that the pulsatile balloon 212 temporarily replicates the function of the native mitral valve. "Temporarily" as used herein refers to a component that has use for a limited period of time and is not permanent. "Replicates" as used herein refers to a prosthetic component or structure that is configured to reproduce the operation or functionality of a native component or structure that the prosthetic component or structure is configured to replace. Thus, in embodiments hereof, the pulsatile balloon 212 temporarily operates as the native heart valve, preventing, or at least limiting backflow or regurgitation through the native mitral valve until the valve member 104 is disposed in the radially expanded configuration within the docking member 102 in the radially expanded configuration at the annulus of the native heart valve. In an example, the heart valve prosthesis 100 is a mitral heart valve prosthesis 100 and the pulsatile balloon 212 prevents, or at least partially restricts backflow or regurgitation through the native mitral valve during diastolic phases of the cardiac cycle of the heart, and allows blood flow through the native mitral valve during systolic phases of the cardiac cycle of the heart.

As shown in the embodiment of FIG. 2, the pulsatile balloon 212 is coaxially disposed under the docking member 102. However, this is not meant to limit the design, and the pulsatile balloon 212 may be disposed at other locations of the inner shaft 208 including but not limited to positions distal of the docking member 102, proximal of the docking member 102 and distal of the valve member 104, proximal of the valve member 104, or any other position suitable for the purposes described herein. Moreover, while the pulsatile balloon 212 is shown in FIG. 2 disposed proximal of the distal tip 210, in another embodiment, the pulsatile balloon 212 may be a portion of the distal tip 210.

Even further, in embodiments wherein the docking member 102 is balloon expandable, the docking member 102 may be mounted on an outer surface of the pulsatile balloon 212, as shown in FIG. 2, and the pulsatile balloon 212 transitioned from the uninflated state to the inflated second state such that the pulsatile balloon 212 expands the docking member 102 to the radially expanded configuration. When in the inflated second state, the pulsatile balloon 212 may have a generally cylindrical or disc shape, however this is not meant to be limiting, and other shapes of the pulsatile balloon 212 in the inflated second state are anticipated. The pulsatile balloon 212 may be a standard construction non-compliant or semi-compliant balloon constructed of any suitable material such as, but not limited to polyethylene terephthalate (PET), nylon, or polyurethane. In embodiments wherein the valve member 104 is balloon expandable, the valve member 104 may be mounted on an outer surface of the pulsatile balloon 212 or alternatively may be mounted on an outer surface of a second balloon (not shown).

Figure 3:
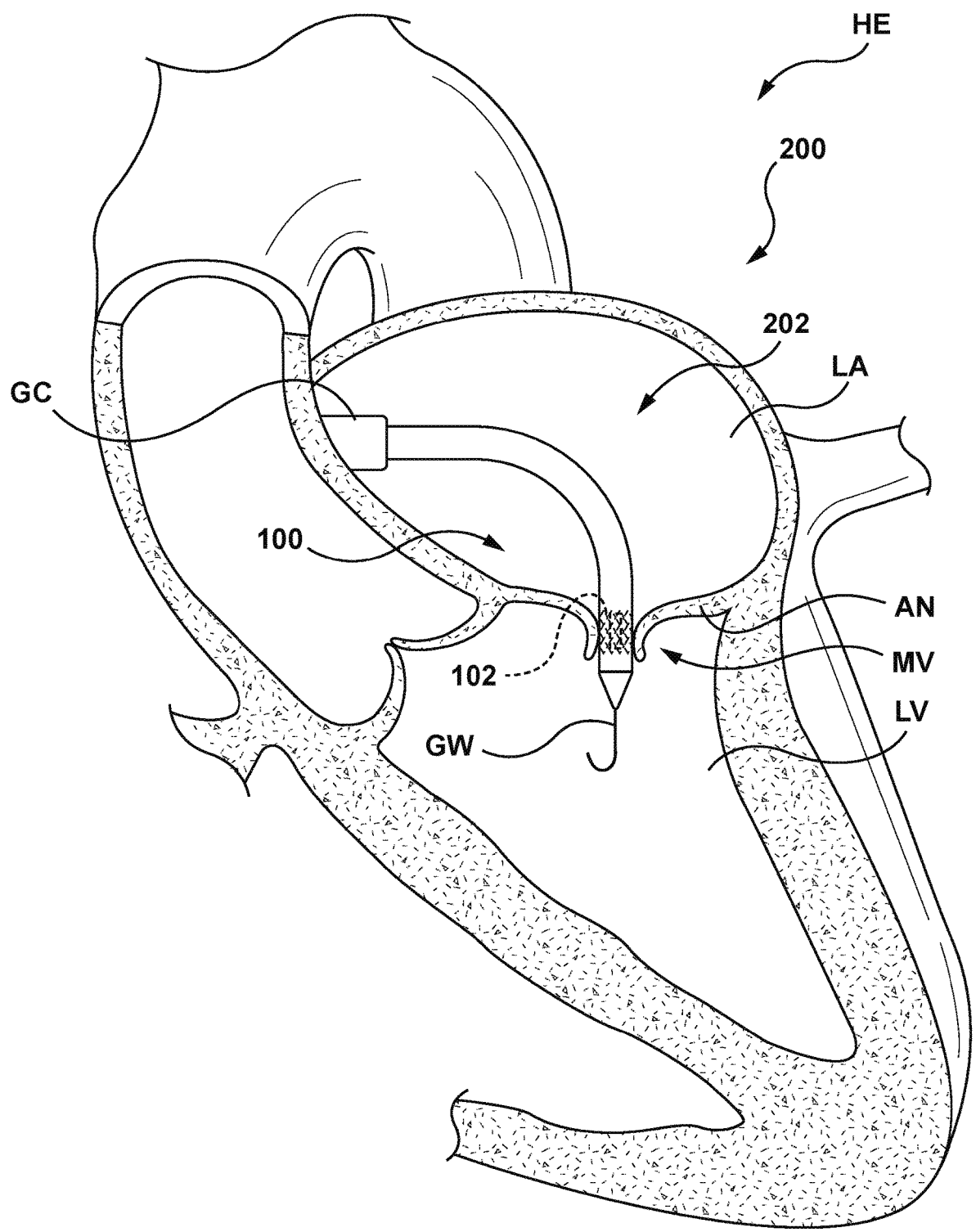
FIG. 3 is an illustration of the delivery system of FIG. 2 in situ, in accordance with an embodiment hereof, wherein the delivery system has been positioned at a native mitral valve via a transseptal approach, the docking member is positioned within an annulus of a native mitral valve, the docking member is in its radially collapsed configuration, and the orifice restriction mechanism is in its delivery state.

FIGS. 3-7 are sectional cut-away views of a heart HE illustrating a method for delivering and positioning the heart valve prosthesis 100 using the delivery system 200 of FIG. 2 in accordance with an embodiment hereof. With reference to FIG. 3, the delivery system 200 is shown after having been introduced into the vasculature via a percutaneous entry point, e.g., the Seldinger technique, and tracked through the vasculature and into the left ventricle LV of the heart HE with the docking member 102 in proximity to and/or apposition within an annulus AN of a native mitral valve MV. Intravascular access to the right atrium may be achieved via a percutaneous access site to femoral venous access up to the inferior venal cava, or other known access routes. Thereafter, a guidewire GW is advanced through the circulatory system, eventually arriving at the heart HE. The guidewire GW is directed into the right atrium, traverses the right atrium and is made to puncture, with the aid of a transseptal needle or pre-existing hole, an atrial septum, thereby entering the left atrium LA. Once the guidewire GW is positioned, the endoluminal entry port and the atrial septum are dilated to permit entry of a guide catheter GC into the left atrium LA. Thereafter, the delivery catheter 202 is advanced over the guidewire GW and through a delivery shaft of the guide catheter GC into the left atrium LA through the punctured atrial septum and positioned proximate or upstream to the native mitral valve MV. Although described as a transfemoral antegrade approach for percutaneously accessing the mitral valve MV, the heart valve prosthesis 100 may be positioned within the desired area of the heart HE via other different methods such as a transseptal antegrade approach via a thoracotomy for accessing the mitral valve MV. In addition, although described with the use of the guide catheter GC and the guidewire GW, in another embodiment hereof the delivery catheter 202 may access the left atrium LA without the use of the guidewire GW and/or the guide catheter GC.

The delivery system 200 is advanced to the site of the native mitral valve MV until the docking member 102 is positioned within the annulus AN of the native mitral valve MV. Referring back to FIG. 2, it will be understood that the delivery system 200 is assembled with the valve member 104 and the docking member 102 of the heart valve prosthesis 100 each in the radially collapsed configuration disposed about the inner shaft 208 at axially spaced apart locations and retained in the radially collapsed configuration by the distal portion 224 of the outer sheath 206. Further, the pulsatile balloon 212 is in the first or uninflated state about the inner shaft 208 and within the distal portion 224 of the outer sheath 206.

Figure 4:
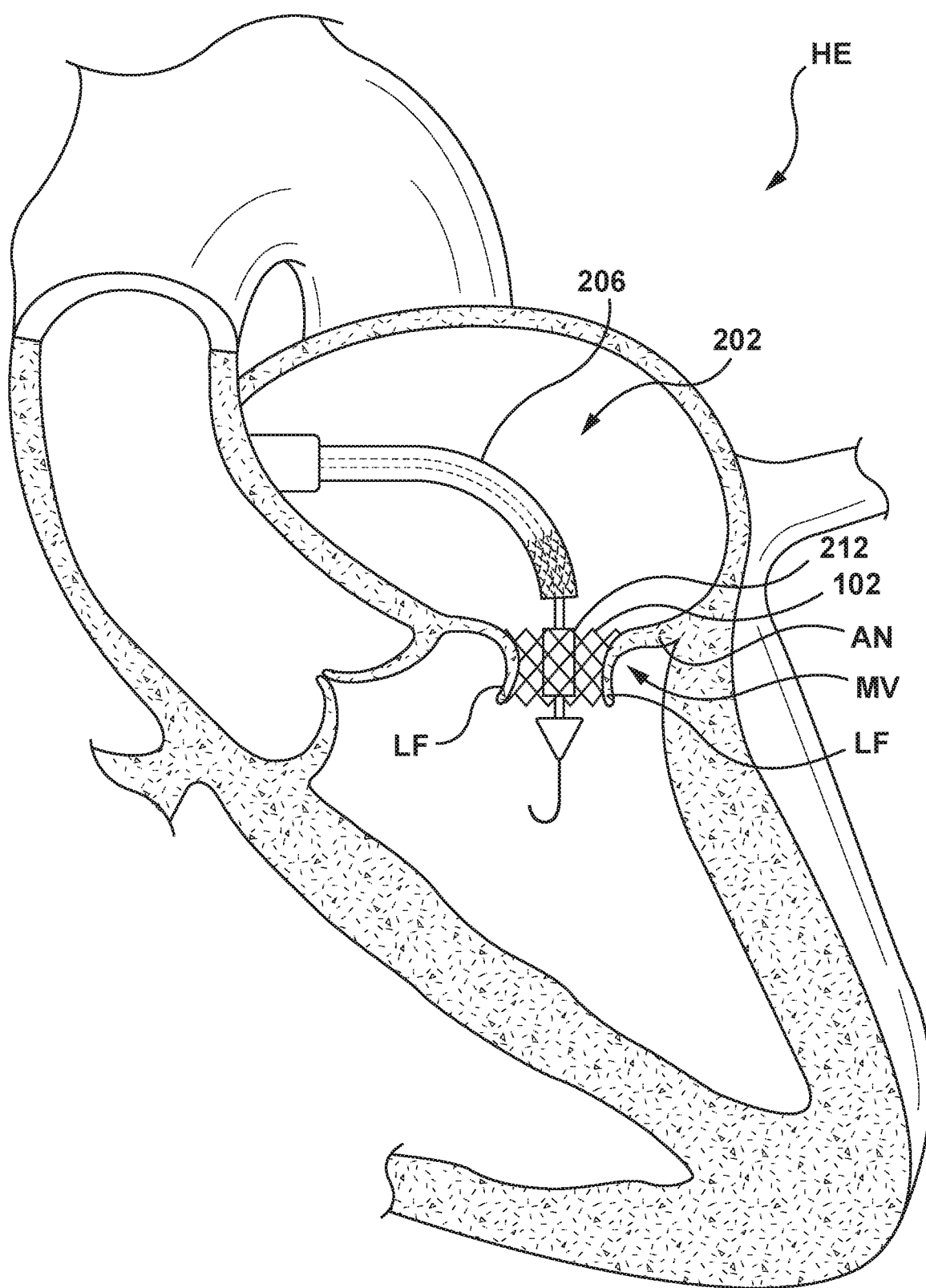
FIG. 4 is an illustration of the delivery system of FIG. 2 in situ, wherein the outer sheath of the delivery catheter has been retracted proximally to release the docking member within the annulus of the native mitral valve, the docking member is in its radially expanded configuration, and the orifice restriction mechanism is in its first state.

In a next delivery step, the handle 204 (not shown in FIGS. 3-7) of the delivery catheter 202 is manipulated such that the outer sheath 206 of the delivery catheter 202 is proximally retracted to release the pulsatile balloon 212 and the docking member 102 disposed thereon. When released, the docking member 102 expands radially outward such that the docking member 102 engages and contacts the tissue at the annulus AN of the native mitral valve MV, as illustrated in FIG. 4. As the docking member 102 radially expands into apposition with the annulus AN of the native mitral valve MV, at least a portion of the docking member 102 engages the leaflets LF of the native mitral valve MV. Once the docking member 102 is deployed, the leaflets LF of the native mitral valve MV are pinned back by the deployed docking member 102 and therefore leaflet function is impaired by the deployed docking member 102.

Figure 5:
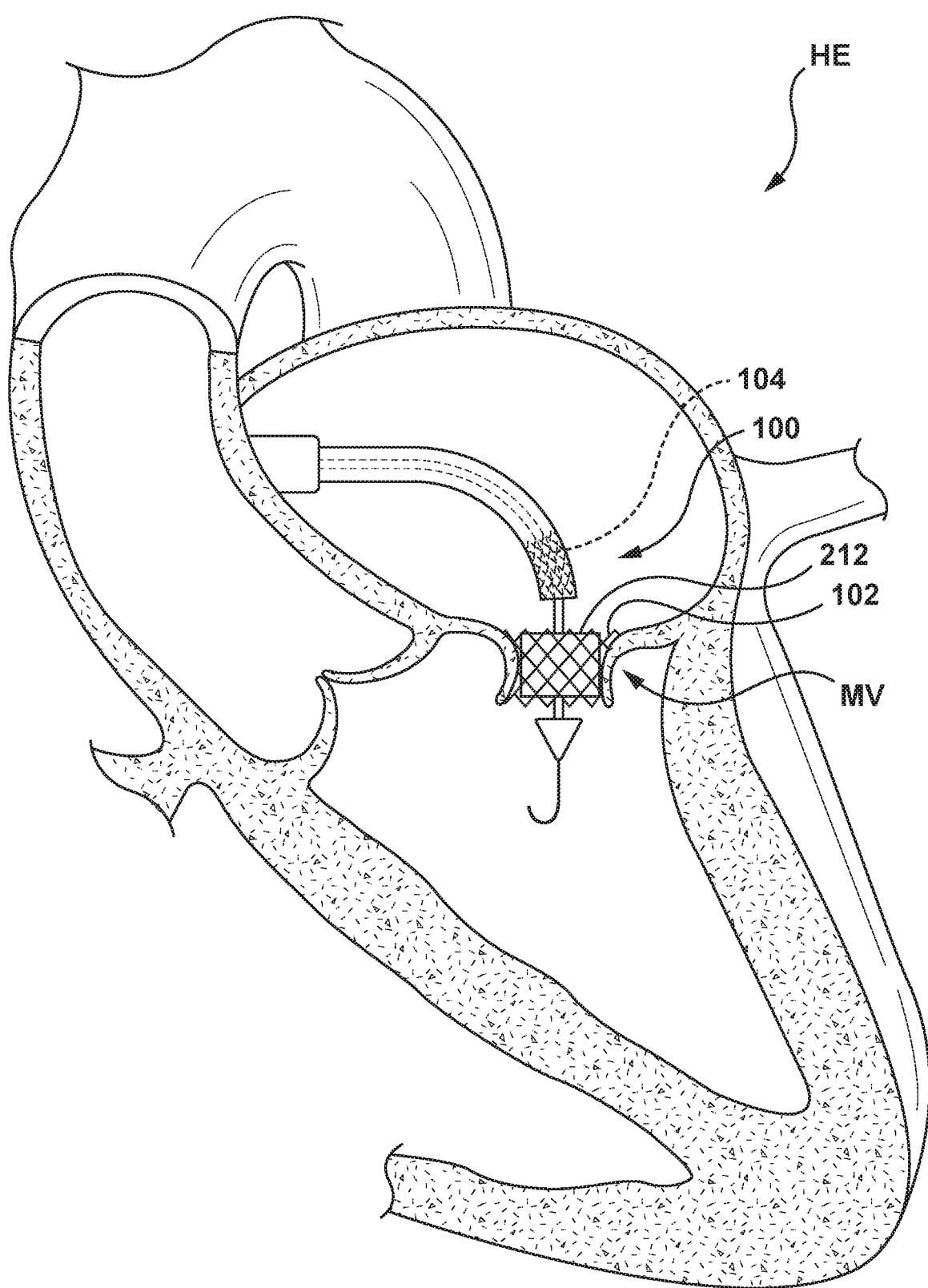
FIG. 5 is an illustration of the delivery system of FIG. 2 in situ, wherein the docking member is positioned within an annulus of a native mitral valve, the docking member is in its radially expanded configuration, and the orifice restriction mechanism is in its inflated second state.

Referring next to FIG. 5, inflation fluid under pressure is cyclically pumped into and out of the inflation lumen 234 (not shown in FIGS. 3-7) and the inflation port 240 (not shown in FIGS. 3-7) in synchronization with the systolic and diastolic phases of the cardiac cycle of the heart, such that the pulsatile balloon 212 continuously transitions or alternates between the inflated second state (as shown in FIG. 5) during systole and the uninflated state (as shown in FIG. 4) during diastole. The inflation fluid may be supplied under pressure, for example, and not by way of limitation, by a pulsatile pump (not shown in FIGS. 3-7) synchronized with the cardiac cycle of the heart. When the pulsatile balloon 212 is in the inflated second state during systole of the heart, the pulsatile balloon 212 blocks, or at least partially restricts blood flow through the deployed docking member 102. When the pulsatile balloon 212 transitions to the uninflated state during diastole of the heart, blood flow is not blocked or is free to flow through the deployed docking member 102. Thus, the continuous transition or alternation of the pulsatile balloon 212 acts as a temporary mitral valve as the valve member 104 of the heart valve prosthesis 100 is prepared to be positioned and deployed.

Figure 6:
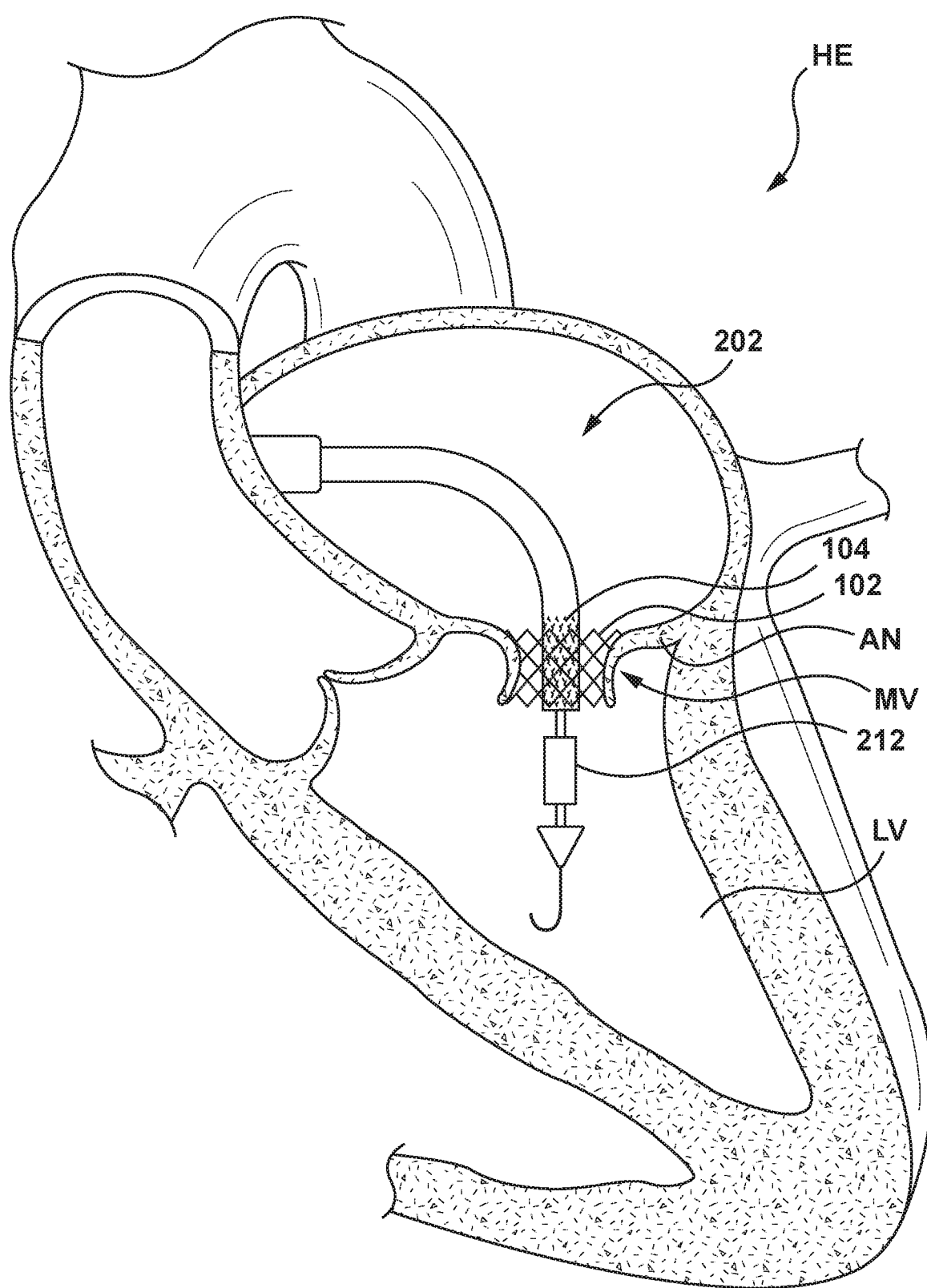
FIG. 6 is an illustration of the delivery system of FIG. 2 in situ, wherein the delivery system has been distally advanced to position the valve member within the docking member, the valve member is in its radially collapsed configuration, and the orifice restriction mechanism is in its first state.

When the clinician is ready to position and deploy the valve member 104 within the docking member 102 at the annulus AN of the native mitral valve MV, the cyclic pressure on the inflation fluid is released and inflation fluid flows out of the pulsatile balloon 212, though the inflation port 240 (not shown in FIGS. 3-7) and the inflation lumen 234 (not shown in FIGS. 3-7) such that the pulsatile balloon 212 transitions to the uninflated state. The delivery catheter 202 is distally advanced to place the valve member 104 within the annulus AN of the native mitral valve MV and within the docking member 102, as shown in FIG. 6. As the delivery catheter 202 is advanced to position the valve member 104 within the docking member 102, the pulsatile balloon 212 (which is disposed over and coupled to the inner shaft 208) is concurrently advanced out of the docking member 102 and into the left ventricle LV of the heart HE.

Figure 7:
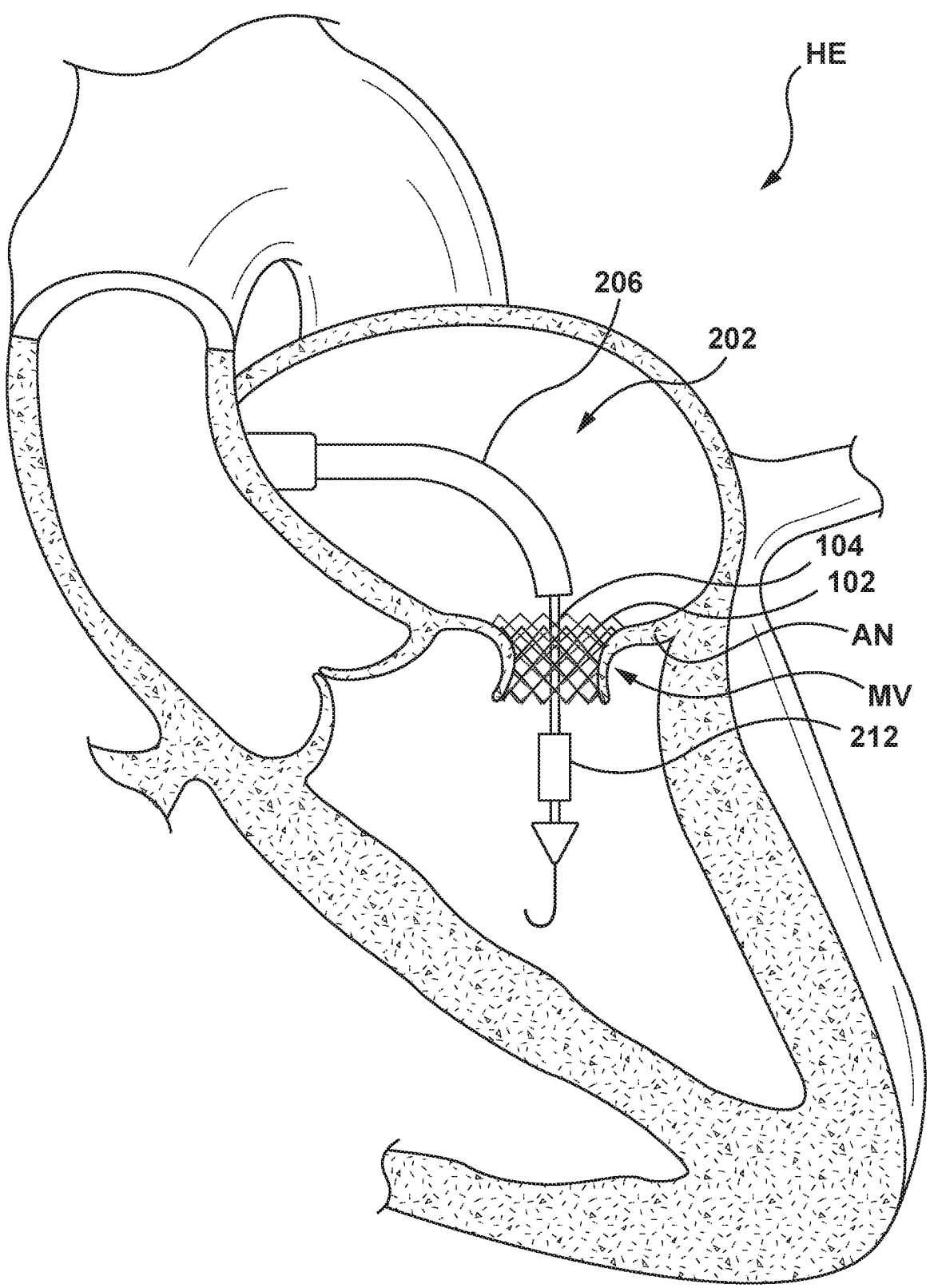
FIG. 7 is an illustration of the delivery system of FIG. 2 in situ, wherein the valve member has been released from the outer sheath of the delivery system, the valve member is in its radially expanded configuration within the docking member, and the orifice restriction mechanism is in its first state.

Referring next to FIG. 7, once the valve member 104 is positioned within the deployed docking member 102, the handle 204 (not shown in FIGS. 3-7) of the delivery catheter 202 is manipulated such that the outer sheath 206 of the delivery catheter 202 is proximally retracted to release the valve member 104. When released, the valve member 104 expands radially to the radially expanded configuration such that the valve member 104 engages and contacts the docking member 102 deployed at the annulus AN of the native mitral valve MV.

Following the radial expansion of the valve member 104, the outer sheath 206 is advanced distally to encapsulate the pulsatile balloon 212 in the uninflated state. Encapsulation of the pulsatile balloon 212 by the outer sheath 206 assists in atraumatic retraction and removal of the delivery catheter 202.

Figure 8:
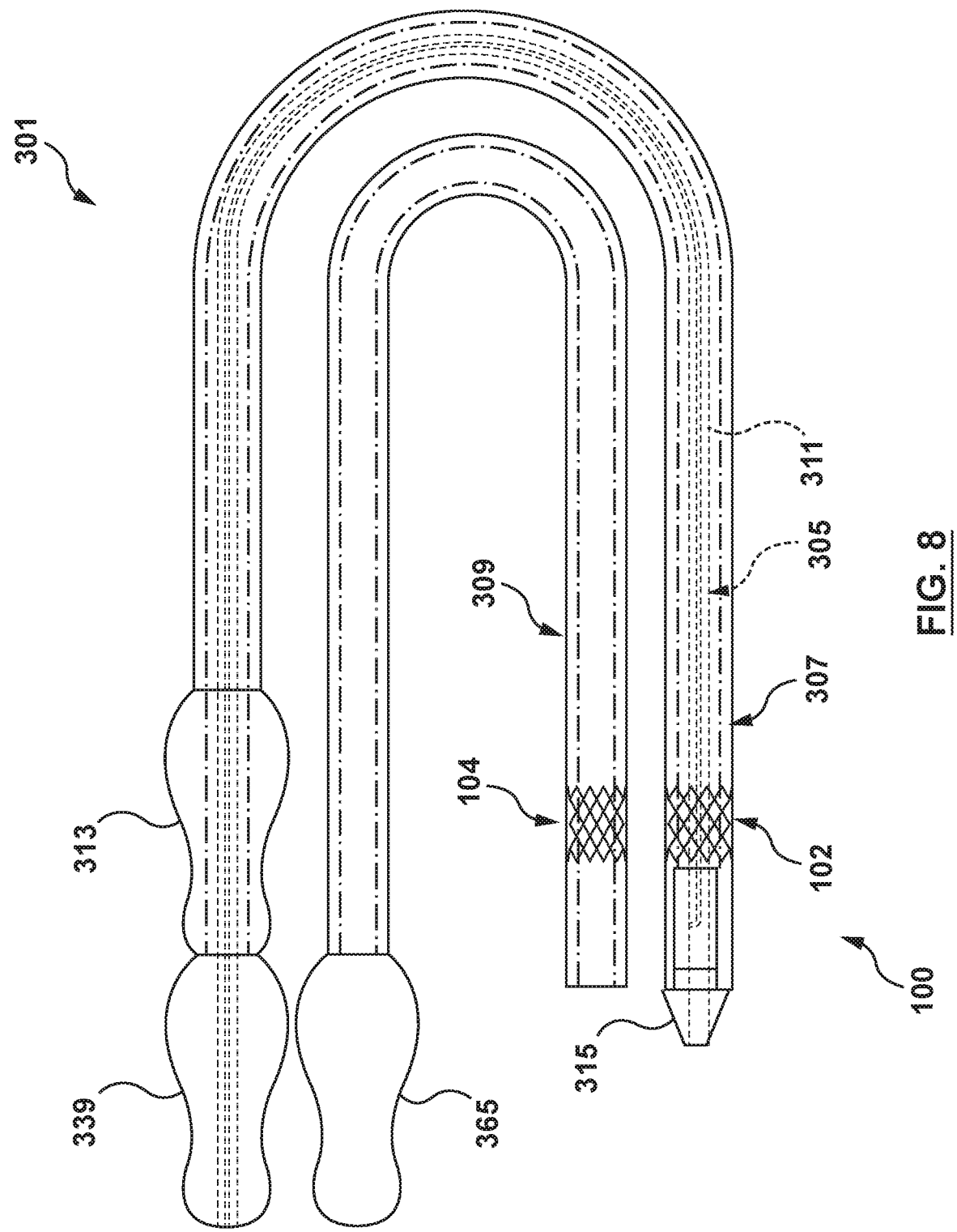
FIG. 8 is a side view illustration of a delivery system configured in accordance with another embodiment hereof, wherein the delivery system includes an orifice restriction mechanism.

In the embodiment described above, the separate components of heart valve prosthesis 100, i.e., the docking member 102 and the valve member 104, are concurrently delivered by a single delivery catheter, i.e., delivery catheter 200. However, in another embodiment hereof illustrated in FIGS. 8-8F, the docking member 102 and the valve member 104 may be separated and sequentially delivered by separate delivery catheters. More particularly, FIGS. 8-8F illustrate a delivery system 301 according to an embodiment hereof in which the temporary valve is an orifice restriction mechanism 303 that is configured to at least partially occlude an annulus of a native heart valve such that the orifice restriction mechanism 303 temporarily replicates, at least partially replicates, the function of leaflets of the native heart valve to prevent regurgitation. FIG. 8 is a side view of the delivery system 301. The delivery system 301 is configured to deliver and implant the heart valve prosthesis 100 described previously herein. The delivery system 301 includes an inner shaft assembly 305 which is shown in greater detail in FIGS. 8A-8D, a docking sheath assembly 307 which is shown in greater detail in FIG. 8E and is configured to deliver the docking member 102, a valve sheath assembly 309 which is shown in greater detail in FIG. 8F and is configured to deliver the valve member 104, and the heart valve prosthesis 100. More particularly, as will be explained in more detail herein, the docking sheath assembly 307 and the valve sheath assembly 309 are configured to be exchangeable over the inner shaft assembly 305. Stated another way, each of the docking sheath assembly 307 and the valve sheath assembly 309 is configured to be coaxially and slidably disposed over an inner shaft 311 of the inner shaft assembly 305. The docking sheath assembly 307 is initially disposed over the inner shaft 311 of the inner shaft assembly 305 and utilized to deliver and implant the docking member 102 of the heart valve prosthesis 100. After the docking member 102 is deployed, the docking sheath assembly 307 is removed and the valve sheath assembly 309 is then distally advanced over the inner shaft 311 of the inner shaft assembly 305. The valve sheath assembly 309 is then utilized to deliver and implant the valve member 104 of the heart valve prosthesis 100. In FIG. 8, the inner shaft assembly 305 is shown with the docking sheath assembly 307 disposed over the inner shaft 311 of the inner shaft assembly 305 and the valve sheath assembly 309 is shown ready to be exchanged with the docking sheath assembly 307.

Each of the inner shaft assembly 305, the docking sheath assembly 307, and the valve sheath assembly 309 will now be described in more detail in turn. More particularly, the inner shaft assembly 305 of the delivery system 301 will be described in more detail with references to FIGS. 8A-8D. As shown in the exploded view of FIG. 8A, the inner shaft assembly 305 of the delivery system 301 includes a handle 313, the inner shaft 311, a distal tip 315, and the orifice restriction mechanism 303. The handle 313 provides a surface for convenient handling and grasping by a user. While the handle 313 of FIGS. 8 and 8A is shown with a cylindrical shape, this is by way of example and not limitation, and other shapes and sizes may be utilized.

Figure 8A:
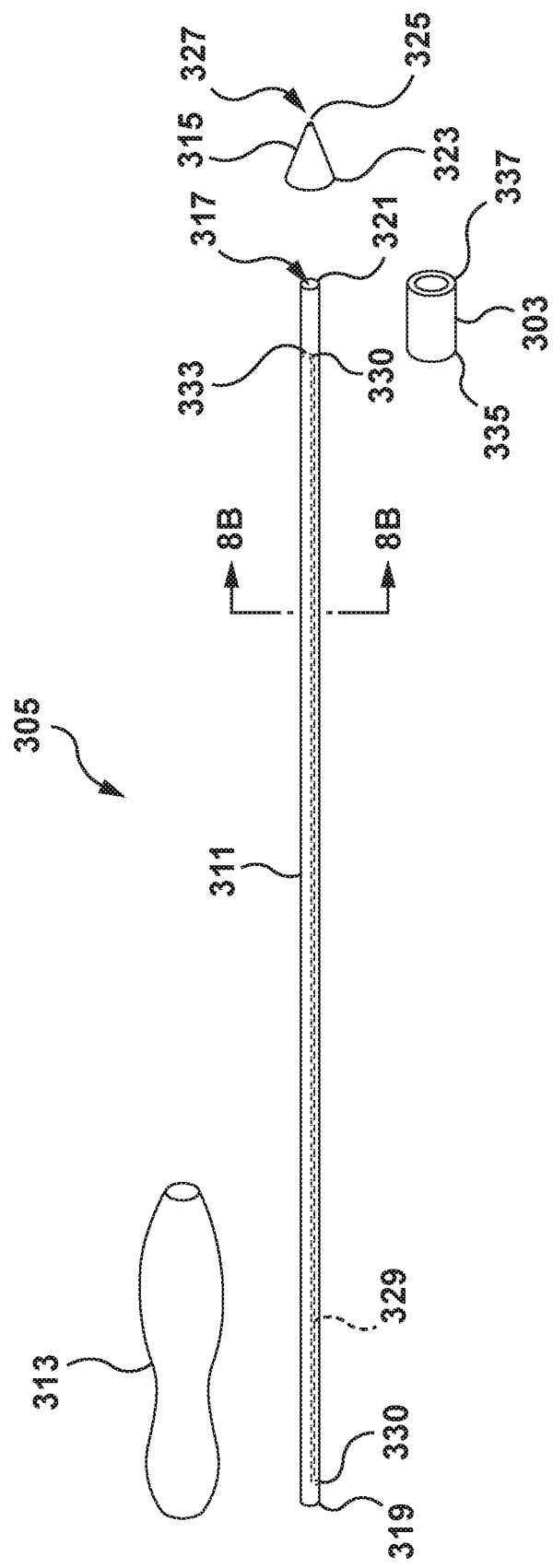
FIG. 8A is an exploded perspective view illustration of an inner shaft assembly of the delivery system of FIG. 8, wherein the orifice restriction mechanism is in its first state.
Figure 8B:
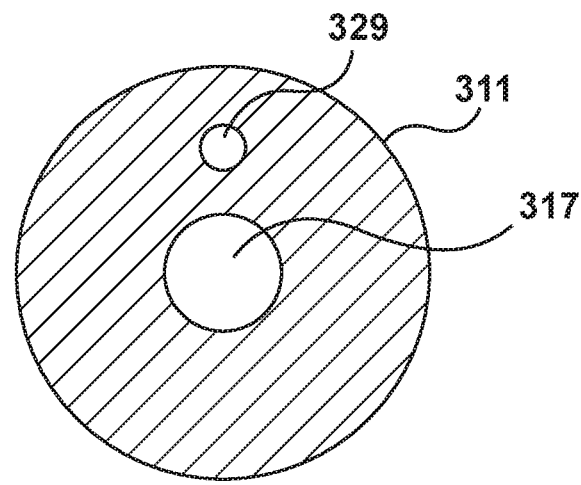
FIG. 8B is a cross-sectional view illustration of an inner shaft of the delivery system of FIG. 8, taken at line 8B-8B of FIG. 8A.
Figure 8C:
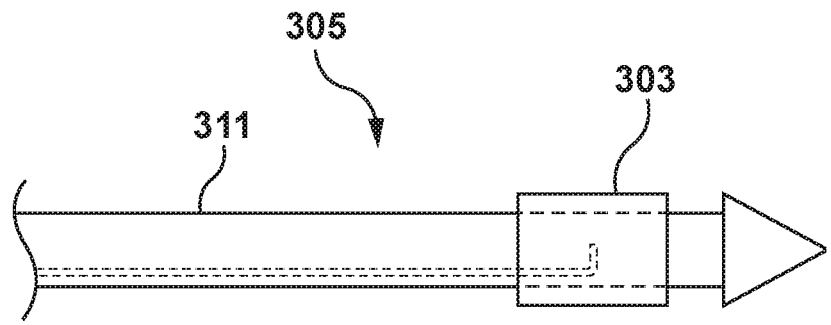
FIG. 8C is a side view illustration of a distal portion of the inner shaft assembly of the delivery system of FIG. 8, wherein the orifice restriction mechanism is in its first state.

The inner shaft 311 of the inner shaft assembly 305 includes a lumen 317 extending from a proximal end 319 to a distal end 321 of the inner shaft 311, as shown in FIG. 8A.

The lumen 317 is sized to receive auxiliary components, such as a guidewire. At least a portion of the inner shaft 311 is configured for fixed connection to the handle 313. In an embodiment, the proximal end 319 of the inner shaft 311 may extend through and be coupled to the handle 313. Although the inner shaft 311 is described herein as a single component, this is by way of example and not limitation, and the inner shaft 311 may include multiple components such as, but not limited to proximal and distal shafts or other components suitable for the purposes described herein. The inner shaft 311 may be formed of materials such as but not limited to polyurethane (e.g. Peliethane®, Elasthane™, Texin®, Tecothane®), polyamide polyether block copolymer (e.g. Pebax®, nylon 12), polyethylene, or other materials suitable for the purposes described herein. The inner shaft 311 may be coupled to the handle 313 by adhesives, bonding, welding, fusing, mechanical connection, or other coupling methods as appropriate.

The distal tip 315 of the inner shaft assembly 305 includes a proximal end 323, a distal end 325, and a lumen 327 extending from the proximal end 323 to the distal end 325. The lumen 327 is sized to receive auxiliary components, such as a guidewire. The proximal end 323 of the distal tip 315 is coupled to the distal end 321 of the inner shaft 311 such that the lumen 327 of the distal tip 315 is longitudinally aligned and in fluid communication with the lumen 317 of the inner shaft 311. Thus, the inner shaft 311 with the distal tip 315 coupled thereto forms a continuous lumen from the proximal end 319 of the inner shaft 311 to the distal end 325 of the distal tip 315. The distal tip 315 may be coupled to the inner shaft 311 by methods such as, but not limited to adhesives, bonding, welding, fusing, mechanical connection, or other coupling methods as appropriate.

Figure 8D:
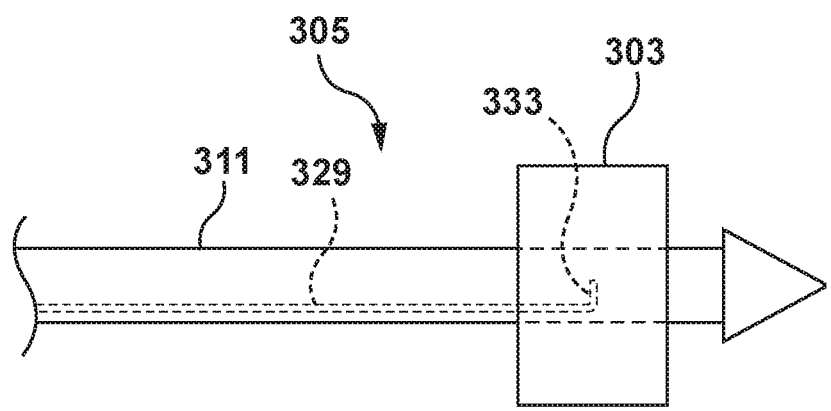
FIG. 8D is a side view illustration of the distal portion of the inner shaft assembly of the delivery system of FIG. 8, wherein the orifice restriction mechanism is in its second state.

The inner shaft 311 further includes an inflation lumen 329, as shown in FIGS. 8-8D. The inflation lumen 329 is defined within a wall of the inner shaft 311, as shown in the cross-sectional view of the inner shaft 311 of FIG. 8B. The inflation lumen 329 includes a proximal end 330 and a distal end 331 in fluid communication with an inflation port 333, as best shown in FIG. 8A. The inflation port 333 is in fluid communication with an interior of the orifice restriction mechanism 303. The inner shaft 311 extends through the handle 313. The inner shaft 311 is fixed relative to the handle 313. The inner shaft 311 may be formed of materials such as but not limited to polyurethane (e.g. Peliethane®, Elasthane™, Texin®, Tecothane®), polyamide polyether block copolymer (e.g. Pebax®, nylon 12), polyethylene, or other materials suitable for the purposes described herein. The inner shaft 311 may be coupled to the handle 313 by adhesives, bonding, welding, fusing, mechanical connection, or other coupling methods as appropriate.

In this embodiment, the orifice restriction mechanism 303 is a balloon. The orifice restriction mechanism 303 may be a standard construction non-compliant or semi-compliant balloon constructed of any suitable material such as, but not limited to polyethylene terephthalate (PET), nylon, or polyurethane. The orifice restriction mechanism 303 includes a proximal end 335 coupled to the inner shaft 311 and a distal end 337 coupled to the inner shaft 311, as shown in FIG. 8A. The orifice restriction mechanism 303 further includes a first or delivery state wherein the orifice restriction mechanism 303 is not inflated, as shown in FIG. 8C and a second or restriction state, wherein the orifice restriction mechanism 303 is inflated, as shown in FIG. 8D. The orifice restriction mechanism 303 transitions from the first state to the second state via inflation fluid delivered under pressure through the inflation lumen 329 of the inner shaft 311 and the inflation port 333 to the interior of the orifice restriction mechanism 303. When in the second state, the orifice restriction mechanism 303 may have a generally cylindrical or disc shape. A diameter of the orifice restriction mechanism 303 in the second state is less than a diameter of a native heart valve within which it is disposed, as described in greater detail below, such that the orifice restriction mechanism 303 will not prevent blood flow though the native heart valve when disposed therein, but rather only restrict the blood flow to minimize regurgitation. In another embodiment hereof, a diameter of the orifice restriction mechanism 303 in the second state is configured to prevent blood flow though the deployed docking member 102 when disposed therein. While described as a cylinder or disc, the orifice restriction mechanism 303 may have other shapes, such as, but not limited to an oval or other shape suitable for the purposes described herein.

In the embodiment of FIG. 8, the orifice restriction mechanism 303 is disposed distal of the docking member 102. However, this is not meant to limit the design, and the orifice restriction mechanism 303 may be disposed at other locations of the inner shaft 311 including but not limited to positions proximal of the docking member 102, coaxially disposed under the docking member 102, or any other position suitable for the purposes described herein. Moreover, while the orifice restriction mechanism 303 is shown in FIG. 8 disposed proximal of the distal tip 315, in another embodiment, the orifice restriction mechanism 303 may be a portion of the distal tip 315.

Figure 9A:
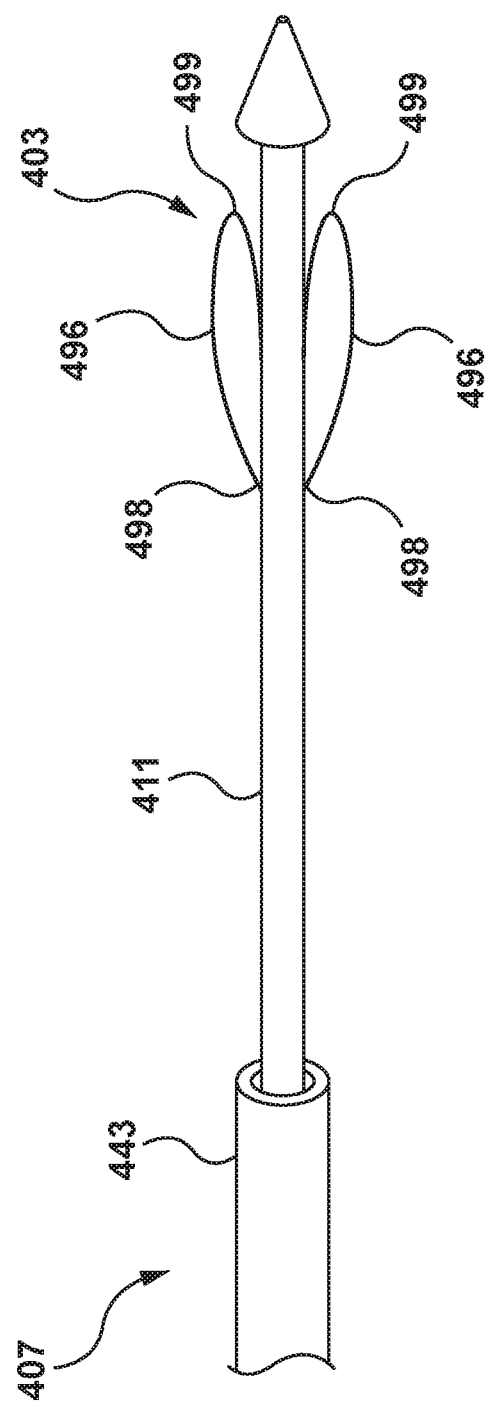
FIG. 9A is a partial perspective view illustration of a distal portion of a delivery system in accordance with another embodiment hereof, wherein an orifice restriction mechanism is a plurality of flaps and is shown in its first state.
Figure 9B:
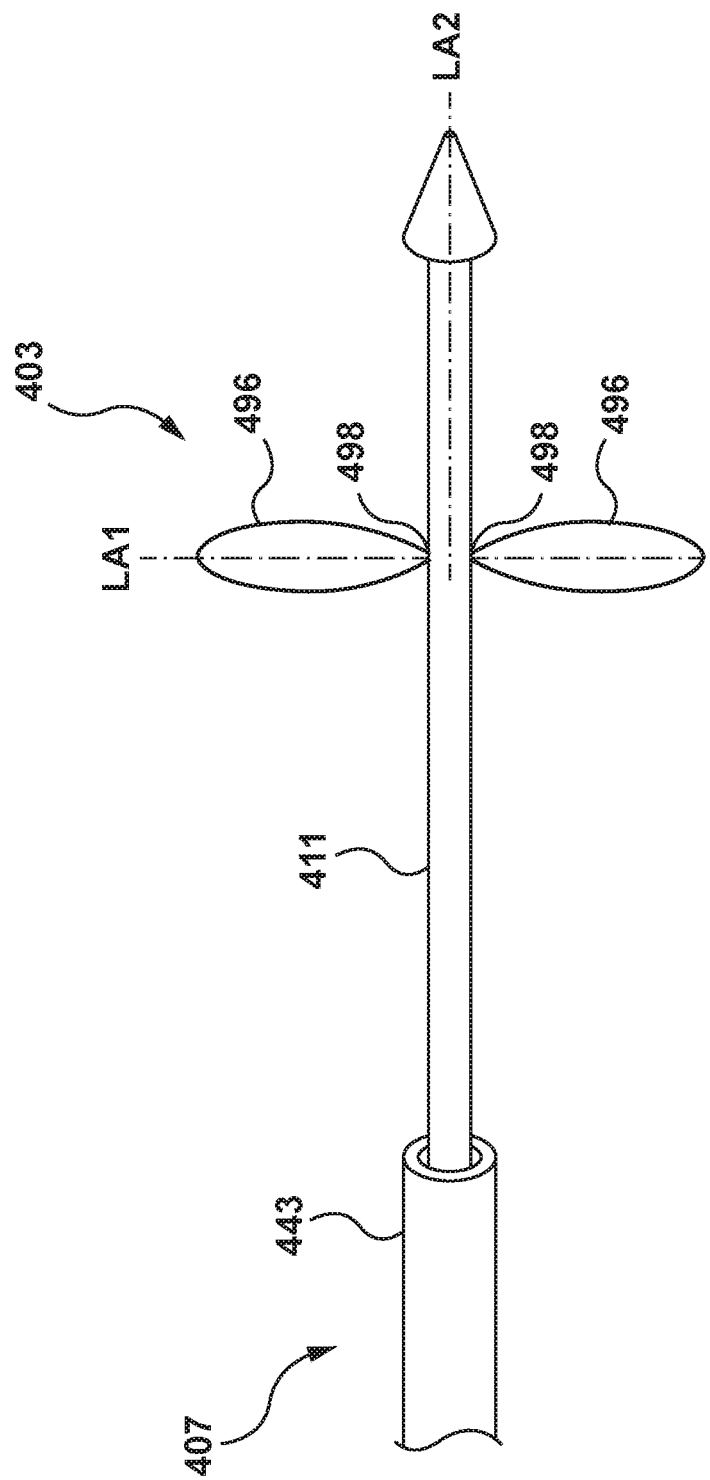
FIG. 9B is a partial perspective view illustration of the distal portion of the delivery system of FIG. 9A, wherein the orifice restriction mechanism is in its second state.

Although the inner shaft assembly 305 is illustrated above with the orifice restriction mechanism 303 as a balloon, the orifice restriction mechanism may be a different structure configured to restrict the blood flow to minimize regurgitation. For example, in another embodiment shown in FIGS. 9A-9B, an orifice restriction mechanism 403 is a plurality of flaps or petals 496 disposed about an outer surface of the inner shaft 411. Each flap 496 includes a first end 498 and a second end 499. The plurality of flaps 496 are spaced radially about a distal portion of the inner shaft 411 with the first end 498 of each flap 496 pivotably coupled, attached or secured to the inner shaft 411 and the second end 499 of each flap 496 free, uncoupled, or unattached relative to the inner shaft 411. Each flap 496 may be of a petal shape, as shown in FIGS. 9A-9B. Alternatively, each flap 496 may be of any shape suitable for the purposes described herein. While shown with two flaps 496, this is not meant to limit the design, and more or fewer flaps 496 may be utilized. In embodiments with a greater number of flaps 496, the plurality of flaps 496 may be disposed about the inner shaft 411 such that each flap 496 overlaps or coapts with an adjacent flap 496. Each flap 496 of the orifice restriction mechanism 403 may be formed of materials such as, but not limited to fabrics, meshes, polyethylene terephthalate (PET), nylon, silicone, or polyurethane. The first end 498 of each flap 496 may be coupled to the inner shaft 411 by methods such as, but not limited to adhesives, welding, fusing, mechanical connection, or other coupling methods as appropriate.

The orifice restriction mechanism 403 includes a first or delivery state in which each flap 496 is disposed with the second end 499 disposed distal of the first end 498 and adjacent the inner shaft 411, as shown in FIG. 9A. With the orifice restriction mechanism 403 in the first state, the orifice restriction mechanism 403 may be retained within the inner sheath 343 of the docking sheath assembly 307 for delivery to a desired treatment site. The orifice restriction mechanism 403 further includes a second or restriction state. When in the second state, each flap 496 is proximally pivoted about the first end 498, to position a first central longitudinal axis LA1 of each flap 496 generally traverse to a second central longitudinal axis LA2 of the inner shaft 411, as shown in FIG. 9B. When disposed within an annulus of a native heart valve, each flap 496 is pivotable between the first state and the second state by blood flow such that backflow, or regurgitation is minimized. In an example, when the orifice restriction mechanism 403 is disposed in an annulus of a native mitral heart valve, the plurality of flaps 496 pivot to the second state during systole and to the first state during diastole of the heart. The length of each flap 496, defined as the distance from the first end 498 to the second end 499, may vary according to application such that a diameter of the orifice restriction mechanism 403 in the second state is less than a diameter of a native heart valve into which it will be disposed and temporarily operate.

Figure 9C:
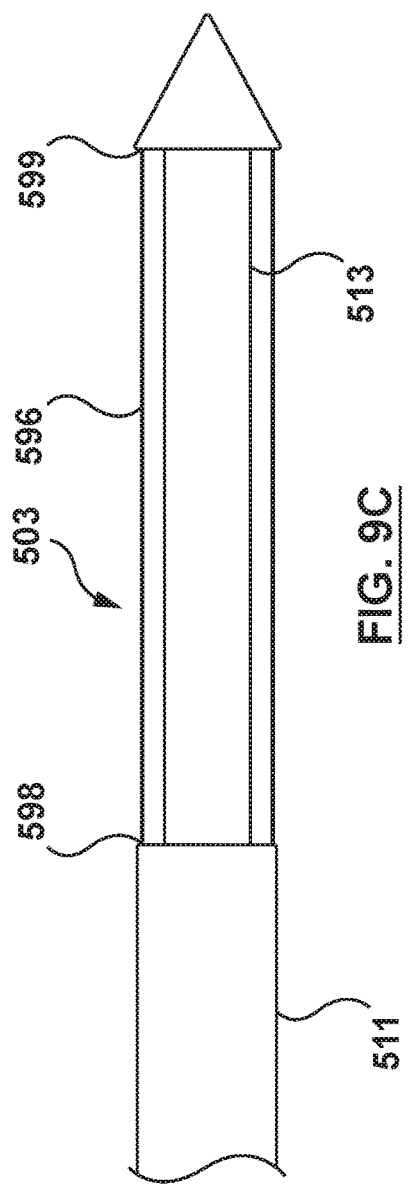
FIG. 9C is a side view illustration of a distal portion of a delivery system in accordance with another embodiment hereof, wherein an orifice restriction mechanism is a radially expandable tube-like member and is shown in its first state.
Figure 9D:
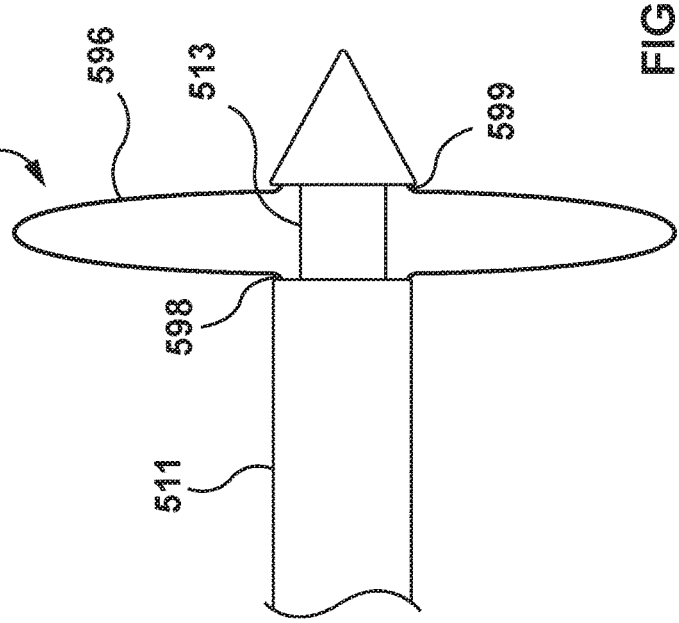
FIG. 9D is a side view illustration of the distal portion of the delivery system of FIG. 9C, wherein the orifice restriction mechanism is in its second state.

In another embodiment shown in FIGS. 9C-9D, an orifice restriction mechanism 503 is a radially expandable tube-like member 596 having a first end 598 coupled, attached or secured to a distal end portion of a first inner shaft 511 and a second end 599 coupled, attached or secured to a distal end portion of a second inner shaft 513, wherein the second inner shaft 513 is slidably received within a lumen 514 of the first inner shaft 511. The orifice restriction member 503 may be radially expandable and radially collapsible by telescopic movement in and out of the second inner shaft 513 relative to the first inner shaft 511. The orifice restriction member 503 may include one or more spines or ribs spaced radially about a portion of the member 503. The orifice restriction member 503 may be formed of materials such as, but not limited to fabrics, meshes, metals, polymers, polyethylene terephthalate (PET), nylon, silicone, or polyurethane. The first end 598 of member 596 may be coupled to the first inner shaft 511 by methods such as, but not limited to adhesives, welding, fusing, mechanical connection, or other coupling methods as appropriate. The second end 599 of member 596 may be coupled to the second inner shaft 511 by methods such as, but not limited to adhesives, welding, fusing, mechanical connection, or other coupling methods as appropriate.

The orifice restriction mechanism 503 includes a first or delivery state in which member 596 is elongated axially, as shown in FIG. 9C. With the orifice restriction mechanism 503 in the first state, the orifice restriction mechanism 503 may be retained within the inner sheath 343 of the docking sheath assembly 307 for delivery to a desired treatment site. The orifice restriction mechanism 503 further includes a second or restriction state. When in the second state, member 596 is expanded radially, as shown in FIG. 9D by proximal movement of the second inner shaft 513 relative to the first inner shaft 511. When disposed within an annulus of a native heart valve, member 596 is changeable between the first state and the second state by movement of the second inner shaft 513 relative to the first inner shaft 511 such that backflow of blood, or regurgitation is minimized. In an example, when the orifice restriction mechanism 503 is disposed in an annulus of a native mitral heart valve, member 596 is switched from the second state during systole to the first state during diastole of the heart. The length of member 596, defined as the distance from the first end 598 to the second end 599, may vary according to application such that a diameter of the orifice restriction mechanism 503 in the second state is less than a diameter of a native heart valve into which it will be disposed and temporarily operate.

The docking sheath assembly 307 of the delivery system 301 will now be described in more detail with reference to the exploded view of FIG. 8E. More particularly, the docking sheath assembly 307 includes a handle 339, an outer sheath 341 and an inner sheath 343. As previously stated, the docking sheath assembly 307 is configured to be coaxially and slidably disposed over the inner shaft 311 of the inner shaft assembly 305 of FIG. 8A and is further configured to deliver and implant the docking member 102 of the heart valve prosthesis 100.

Figure 8E:
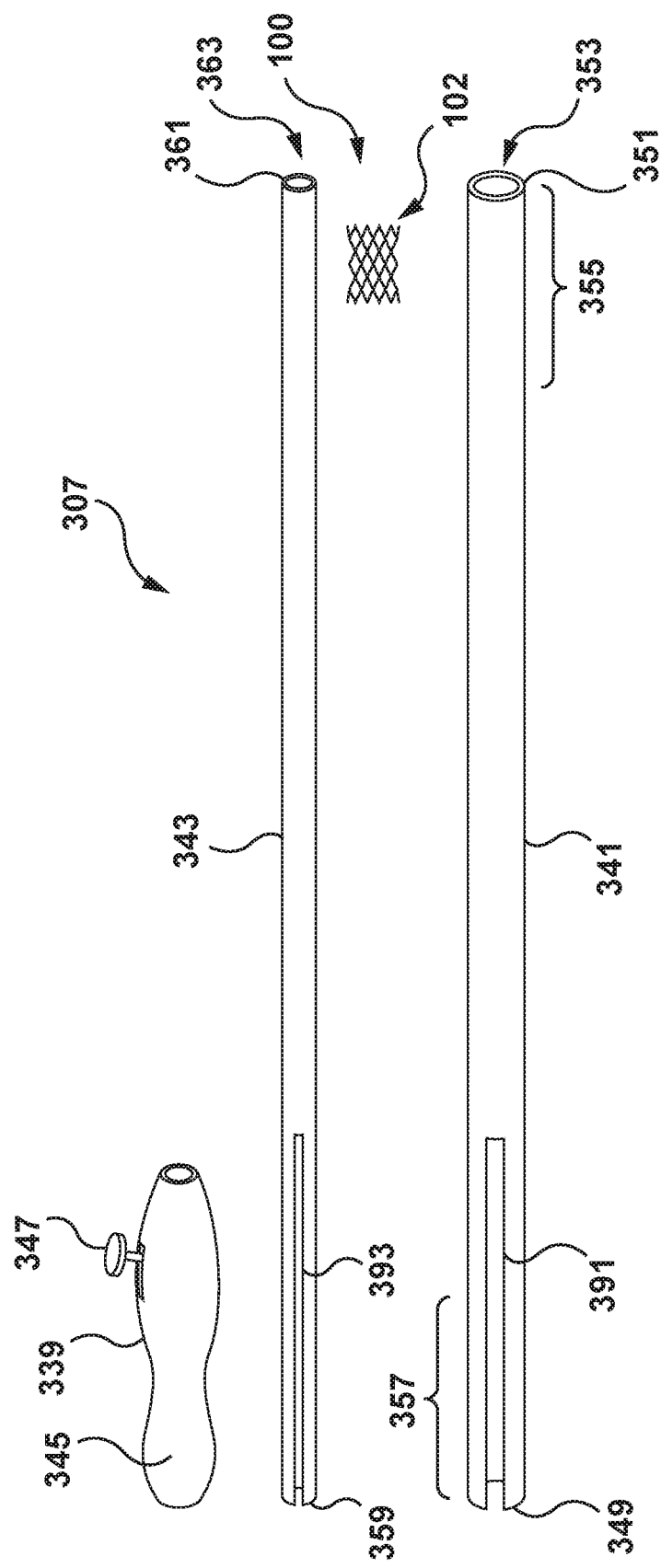
FIG. 8E is an exploded perspective view illustration of a docking sheath assembly of the delivery system of FIG. 8, wherein a docking member of the heart valve prosthesis of FIG. 1 is mounted at a distal portion thereof, the docking member being shown in its radially collapsed configuration for delivery.
Figure 8F:
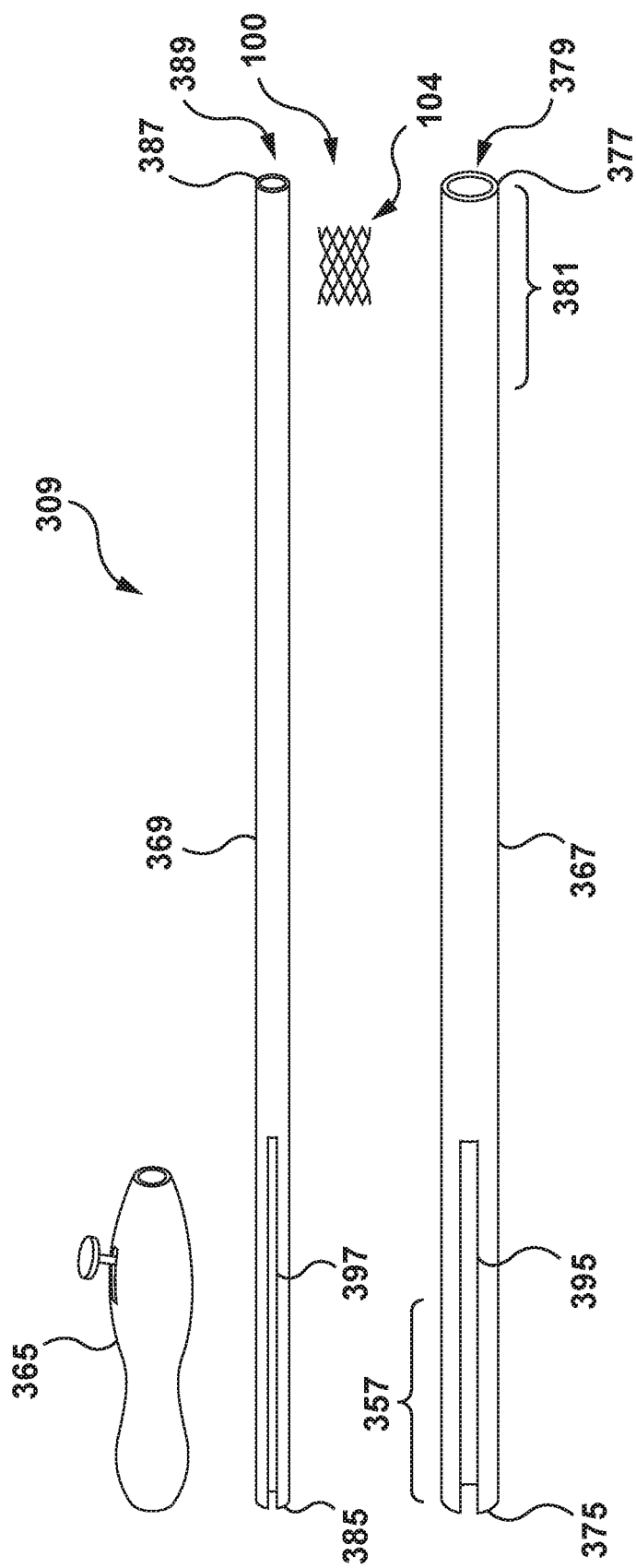
FIG. 8F is an exploded perspective view illustration of a valve sheath assembly of the delivery system of FIG. 8, wherein a valve member of the heart valve prosthesis of FIG. 1 is mounted at a distal portion thereof, the valve member being shown in its radially collapsed configuration for delivery.

As shown in FIG. 8E, the handle 339 includes a housing 345 and an actuation mechanism 347 for interfacing by a user. The handle 339 provides a surface for convenient handling and grasping by a user, and while the handle 339 of FIG. 8E is shown with a cylindrical shape, this is by way of example and not limitation, and other shapes and sizes may be used based on the application requirements. Further, while the handle 339 is shown with a specific style of actuation mechanisms 347, this is also by way of example and not limitation, and various actuation mechanisms may be utilized including, but not limited to an axially-slidable lever, a rotary rack and pinion gear, or other applicable actuation mechanisms.

Also shown in FIG. 8E, the outer sheath 341 includes a proximal end 349, a distal end 351, and a lumen 353 extending from the proximal end 349 to the distal end 351 of the outer sheath 341. The lumen 353 is sized to receive the inner sheath 343. A distal portion 355 of the outer sheath 341 is configured to retain the docking member 102 of the heart valve prosthesis 100 in the radially collapsed configuration for delivery to the desired treatment location. While the distal portion 355 is described herein as a distal portion of the outer sheath 341, in an embodiment, the distal portion 355 may be a separate component, such as a capsule, coupled to the distal end 351 of the outer sheath 341. Moreover, although the outer sheath 341 is described herein as a single component, this is by way of example and not limitation, and the outer sheath 341 may include multiple components such as, but not limited to proximal and distal shafts, or other components suitable for the purposes described herein. The proximal end 349 of the outer sheath 341 is configured for fixed connection to the handle 339. In an embodiment, the proximal end 349 of the outer sheath 341 may extend proximally into the housing 345 of the handle 339 and a proximal portion 357 of the outer sheath 341 may be operably coupled to the actuation mechanism 347 of the handle 339. The proximal portion 357 is operably coupled to the actuation mechanism 347 such that movement of the actuation mechanism 347 causes the outer sheath 341 and the distal portion/distal portion 355 to move relative to the inner sheath 343 and the handle 339. However, if the actuation mechanism 347 is not moved and the handle 339 is moved, the outer sheath 341 moves with the handle 339, not relative to the handle 339. The outer sheath 341 may be constructed of materials such as, but not limited to polyurethane, polyether block amide (PEBA), polyamide, polyether block copolymer, polyethylene, or other materials suitable for the purposes of the present disclosure. The proximal portion 357 of the outer sheath 341 may be coupled to the actuation mechanism 347, for example, and not by way of limitation by adhesives, welding, clamping, linkages or other coupling methods as appropriate.

As further shown in FIG. 8E, the inner sheath 343 of the docking sheath assembly 307 extends within the outer sheath 341 and includes a proximal end 359, a distal end 361, and the lumen 363 extending from the proximal end 359 to the distal end 361 of the inner sheath 343. The lumen 363 is sized to receive the inner shaft assembly 305. A distal portion of the inner sheath 343 is configured to cover or encapsulate the orifice restriction mechanism 303 in the first state for delivery to the desired treatment location. The proximal end 359 of the inner sheath 343 is configured for fixed connection to the handle 339. In an embodiment, the proximal end 359 of the inner sheath 343 may extend through the housing 345 and be coupled to the handle 339. During sliding or longitudinal movement of the outer sheath 341 relative thereto, the inner sheath 343 is fixed relative to the handle 339. Although the inner sheath 343 is described herein as a single component, this is by way of example and not limitation, and the inner sheath 343 may include multiple components such as, but not limited to proximal and distal shafts, or other components suitable for the purposes described herein. The inner sheath 343 may be formed of materials such as but not limited to polyurethane (e.g. Peliethane®, Elasthane™, Texin®, Tecothane®), polyamide polyether block copolymer (e.g. Pebax®, nylon 12), polyethylene, or other materials suitable for the purposes described herein. The inner sheath 343 may be coupled to the handle 339 by adhesives, bonding, welding, fusing, mechanical connection, or other coupling methods as appropriate.

The outer sheath 341 may further include a slot 391 disposed through a wall of the outer sheath 341, the slot 391 extending distally from the proximal end 349 of the outer sheath 341 over a proximal portion thereof. The inner sheath 343 may further include a slot 393 disposed through a wall of the inner sheath 343. The slot 393 extends from the proximal end 359 of the inner sheath 343 extending distally over a proximal portion thereof. Each of the slots 391 and 393 is configured to provide access to the inflation lumen 329 of the inner shaft 311 when the inner shaft 311 is received within the lumen 363 of the inner sheath 343 of the docking sheath assembly 307. Slots 391, 393 are longitudinally and circumferentially aligned in order to provide access to the inflation lumen 329 of the inner shaft 311 for connection to a source of inflation. In other embodiments, other mechanisms may be provided in order to provide access to the inflation lumen 329 of the inner shaft 311 for connection to a source of inflation.

The valve sheath assembly 309 of the delivery system 301 will now be described in more detail with reference to the exploded view of FIG. 8F. More particularly, the valve sheath assembly 309 is similar to the docking sheath assembly 307 except that the valve sheath assembly 309 is configured to deliver and implant the valve member 104 of the heart valve prosthesis 100 rather than the docking member 102 of heart valve prosthesis 100. The valve sheath assembly 309 includes a handle 365, an outer sheath 367 and an inner sheath 369 which are similar to the handle 339, the outer sheath 341, and the inner sheath 343, respectively, of the docking sheath assembly 307. Therefore, details of their construction and alternatives will not be repeated. The outer sheath 367 of the valve sheath assembly 309 includes a proximal end 375, a distal end 377, and a lumen 379 extending from the proximal end 375 to the distal end 377 of the outer sheath 367. A distal portion 381 of the outer sheath 367 is configured to retain the valve member 104 of the heart valve prosthesis 100 in the radially collapsed configuration for delivery to the desired treatment location. The inner sheath 369 of the valve sheath assembly 309 includes a proximal end 385, a distal end 387, and a lumen 389 extending from the proximal end 385 to the distal end 387 of the inner sheath 369. The lumen 389 of the inner sheath 369 is sized to receive the inner shaft 311 of the inner shaft assembly 305. The valve sheath assembly 309 may further include a slot 395 through a wall of the outer sheath 367 and a slot 397 through a wall in the inner sheath 369, which are similar to the slots 391 and 393 of the docking sheath assembly 307, described previously. Each of the slots 395 and 397 is configured to provide access to the inflation lumen 329 of the inner shaft 311 when the inner shaft 311 is received within the lumen 389 of the inner sheath 369 of the valve sheath assembly 309. Slots 395, 397 are longitudinally and circumferentially aligned in order to provide access to the inflation lumen 329 of the inner shaft 311 for connection to a source of inflation.

Figure 10:
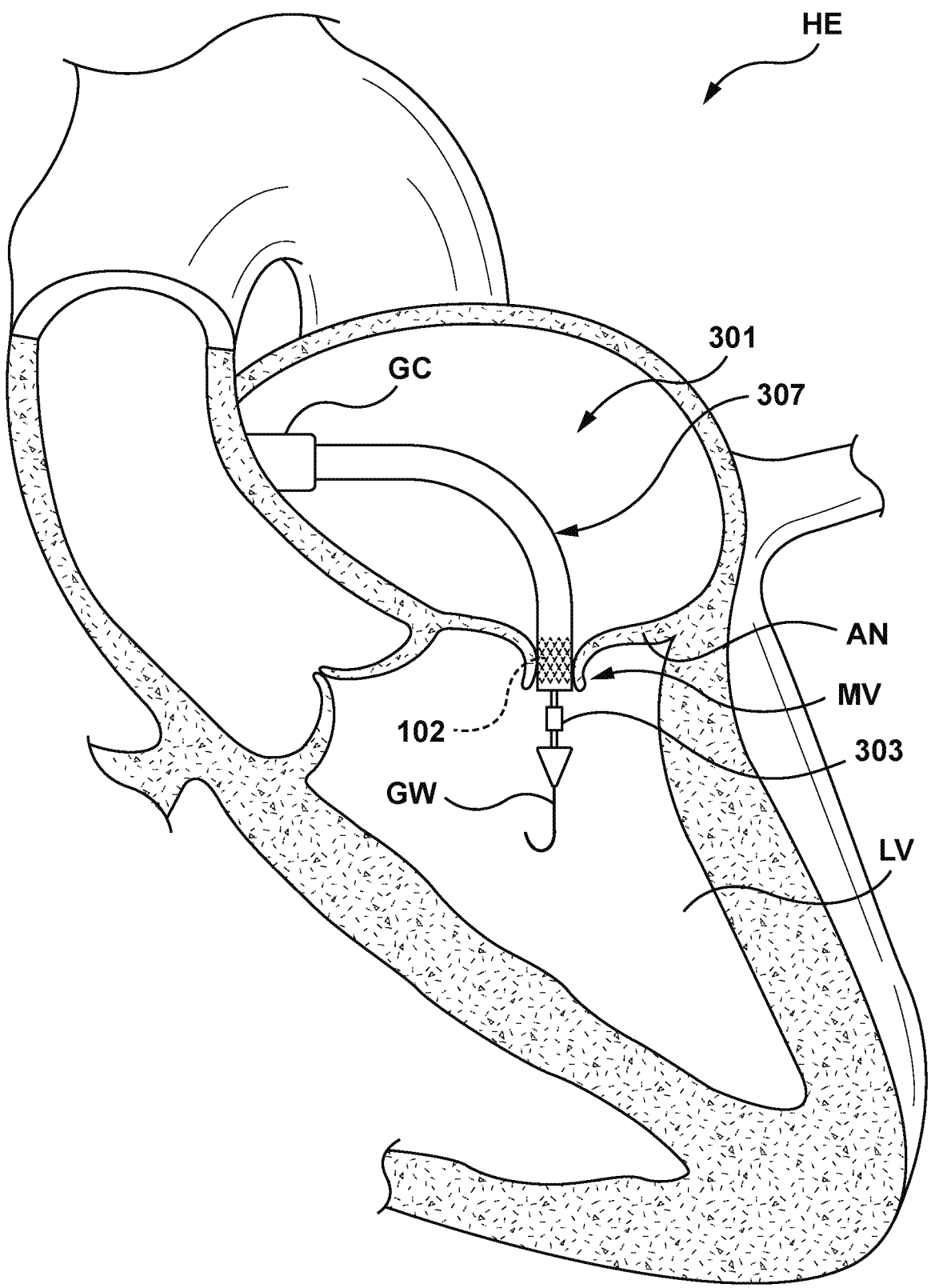
FIG. 10 is an illustration of the delivery system of FIG. 8 in situ, in accordance with embodiment hereof, wherein the delivery system has been positioned at a native mitral valve via a transseptal approach, the docking member is positioned within an annulus of a native mitral valve, the docking member is in its radially collapsed configuration, and the orifice restriction mechanism is in its first state.

FIGS. 10-16 are sectional cut-away views of a heart HE illustrating a method for delivering and positioning the heart valve prosthesis 100 using the delivery system 301 of FIG. 8 in accordance with an embodiment hereof. With reference to FIG. 10, the delivery system 301 is shown after having been introduced via the Seldinger technique or other suitable percutaneous entry technique into the vasculature. Intravascular access may be achieved as described previously with the method of FIGS. 3-7.

In FIG. 10, the delivery system 301 has been tracked through the vasculature and into the left ventricle LV of the heart HE. As previously described herein, the delivery system 301 is initially assembled with the docking sheath assembly 307 coaxially disposed over the inner shaft 311 of the inner shaft assembly 305. The docking member 102 is in the radially collapsed configuration disposed about the inner sheath 343 of the docking sheath assembly 307 and retained in the radially collapsed configuration by the distal portion 355 of the outer sheath 341 of the docking sheath assembly 307. The orifice restriction mechanism 303 is in the first state about the inner shaft 311 of the inner shaft assembly 305 and retained within a distal portion of the lumen 363 of the inner sheath 343 of the docking sheath assembly 307. With reference to FIG. 10, the orifice restriction mechanism 303 has been positioned in the left ventricle LV adjacent the annulus AN of the native mitral valve MV and the docking sheath assembly 307 has been proximally retracted such that the inner sheath 343 (obscured from FIG. 10 by the outer sheath 341) of the docking sheath assembly 307 uncovers the orifice restriction mechanism 303 which is in the first state. The docking sheath assembly 307 has been proximally retracted until the docking member 102 is positioned within the annulus AN of the native mitral valve MV.

Figure 11:
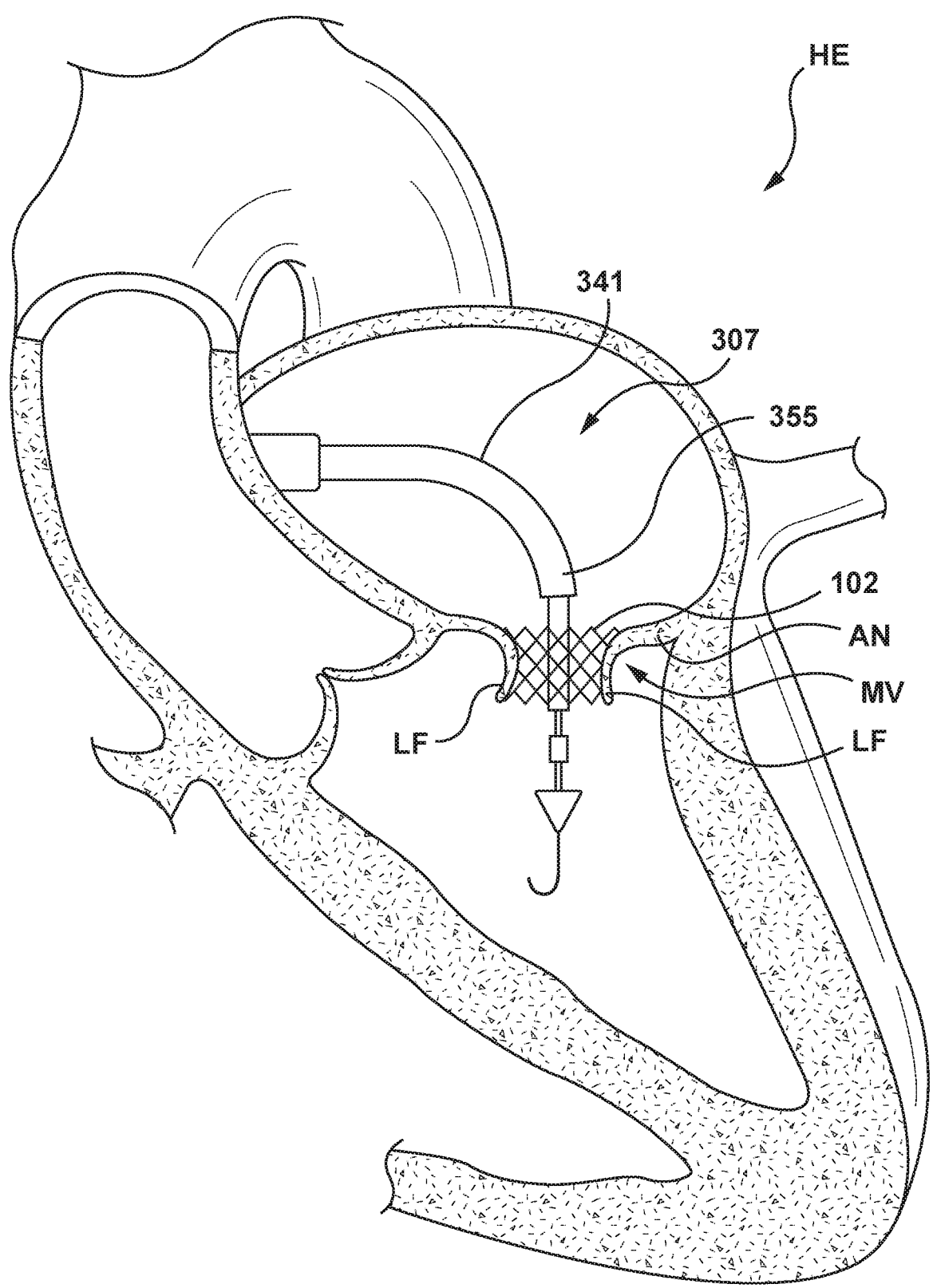
FIG. 11 is an illustration of the delivery system of FIG. 8 in situ, wherein the docking member has been released from the outer sheath of the docking sheath assembly and is positioned within the annulus of the native mitral valve in its radially expanded configuration.

With reference now to FIG. 11, the handle 339 (not shown in FIGS. 10-16) of the docking sheath assembly 307 is then manipulated to retract the outer sheath 341 of the docking sheath assembly 307, thereby releasing the docking member 102 from the distal portion 355 of the outer sheath 341. When released from the distal portion 355, the docking member 102 expands radially outward such that the docking member 102 engages tissue at the annulus AN of the native mitral valve MV. As the docking member 102 radially expands into apposition with the annulus of the native mitral valve, at least a portion of the docking member 102 engages the leaflets LF of the native mitral valve MV. Once the docking member 102 is deployed, the leaflets LF of the native mitral valve MV are pinned back by the deployed docking member 102 and therefore leaflet function is impaired by the deployed docking member 102.

Figure 12:
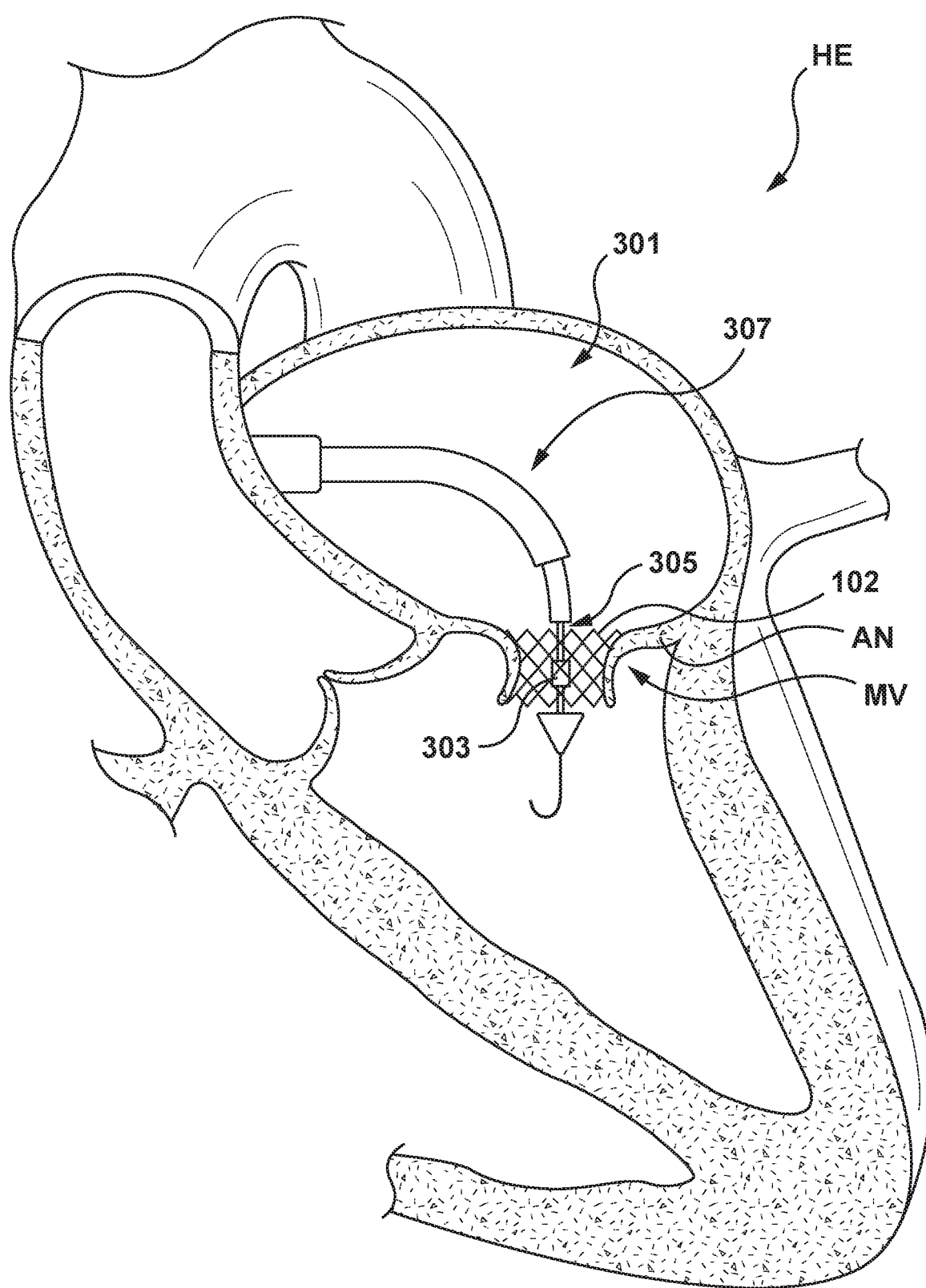
FIG. 12 is an illustration of the delivery system of FIG. 8 in situ, wherein the orifice restriction mechanism has been positioned within the docking member, and the orifice restriction mechanism is in its first state.

As illustrated next in FIG. 12, with the docking member 102 radially expanded within the annulus AN of the native mitral valve MV, the delivery system 301, including the inner shaft assembly 305 and the docking sheath assembly 307, is proximally retracted to position the orifice restriction mechanism 303 in the first state within the docking member 102. In other embodiments, only the inner shaft assembly 305 may be proximally retracted to position the orifice restriction mechanism 303 in the first state within the docking member 102.

Figure 13:
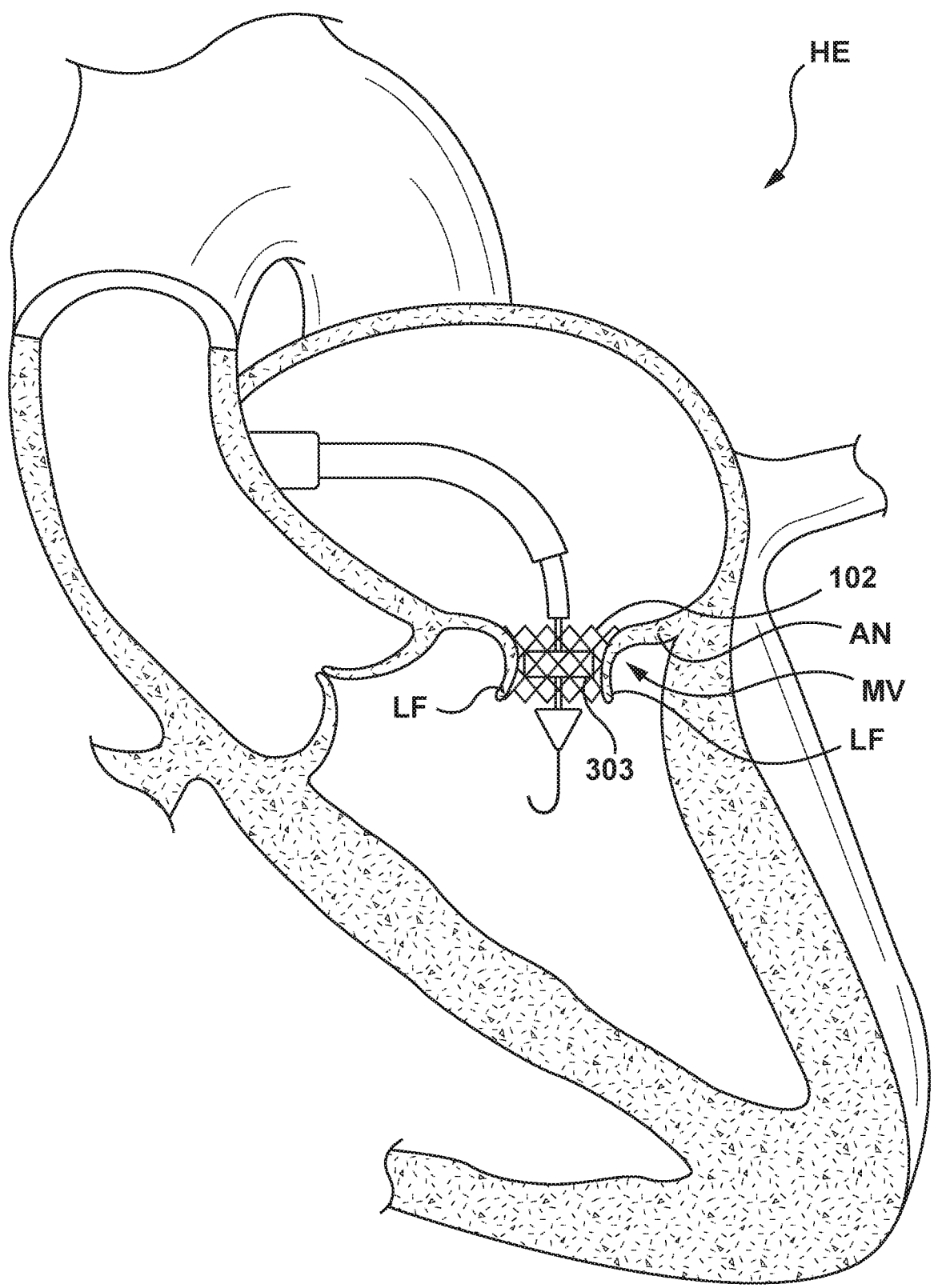
FIG. 13 is an illustration of the delivery system of FIG. 8 in situ, wherein the orifice restriction mechanism has been positioned within the docking member, and the orifice restriction mechanism is in its second state.

Once the orifice restriction mechanism 303 is positioned within the deployed docking member 102, inflation fluid under pressure is pumped into the inflation lumen 329 (not shown in FIGS. 10-16) and the inflation port 333 (not shown in FIGS. 10-16) to transition the orifice restriction mechanism 303 from the first state to the second state within the docking member 102, as shown in FIG. 13. When the orifice restriction mechanism 303 transitions to the second state, blood flow is at least partially restricted through the native mitral valve MV. More specifically, the orifice restriction mechanism 303 temporarily replicates, or at least partially replicates, the function of leaflets LF of the native mitral valve MV to prevent regurgitation as the valve member 104 of the heart valve prosthesis 100 is prepared to be positioned and deployed.

Figure 14:
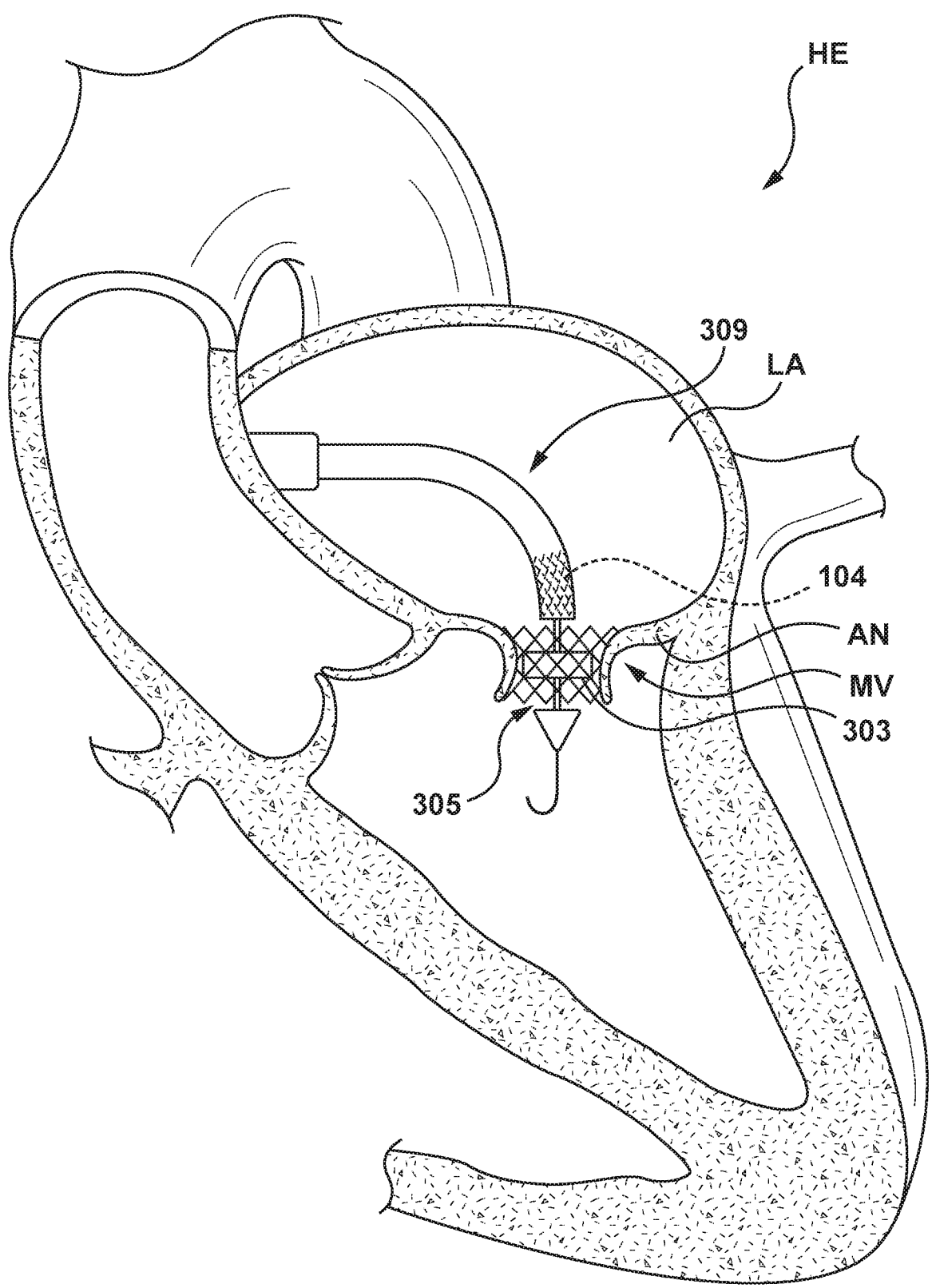
FIG. 14 is an illustration of the delivery system of FIG. 8 in situ, wherein the docking sheath assembly has been exchanged for the valve sheath assembly, and the valve sheath assembly has been distally advanced to position the valve member in the left atrium proximate to the native mitral valve.

With the orifice restriction mechanism 303 in the second state within the deployed docking member 102, the inner shaft assembly 305 remains stationary and is not moved while the docking sheath assembly 307 is proximally retracted, removed, and exchanged with the valve sheath assembly 309. More specifically, the docking sheath assembly 307 is proximally retracted and removed, the valve sheath assembly 309 is then positioned to be coaxially disposed over the inner shaft assembly 305, and the valve sheath assembly 309 is then advanced distally over the inner shaft assembly 305 to position the valve member 104 within the left atrium LA proximate the native mitral valve MV as shown in FIG. 14.

Figure 15:
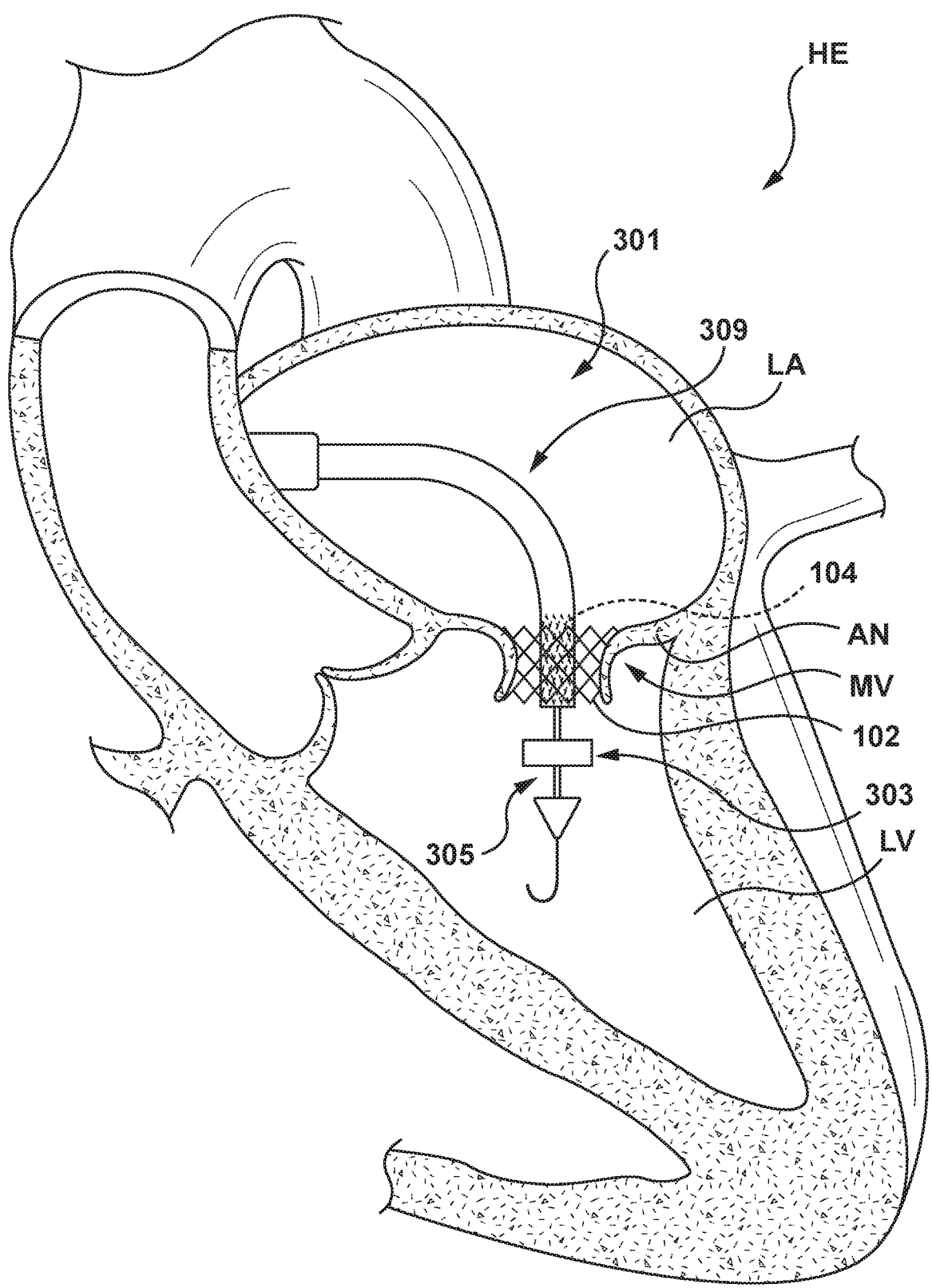
FIG. 15 is an illustration of the delivery system of FIG. 8 in situ, wherein the delivery system has been distally advanced to position the valve member within the docking member, the valve member is in its radially collapsed configuration, and the orifice restriction mechanism is in its second state.

Referencing FIG. 15, when the clinician is ready to position and deploy the valve component 104 within the docking member 102 at the annulus AN of the native mitral valve MV, the delivery system 301, including the inner shaft assembly 305 and the valve sheath assembly 309, is distally advanced to place the valve member 104 within the deployed docking member 102. As the delivery system 301 is advanced, the orifice restriction mechanism 303 is distally advanced out of the annulus AN of the native mitral valve MV and into the left ventricle LV.

Figure 16:
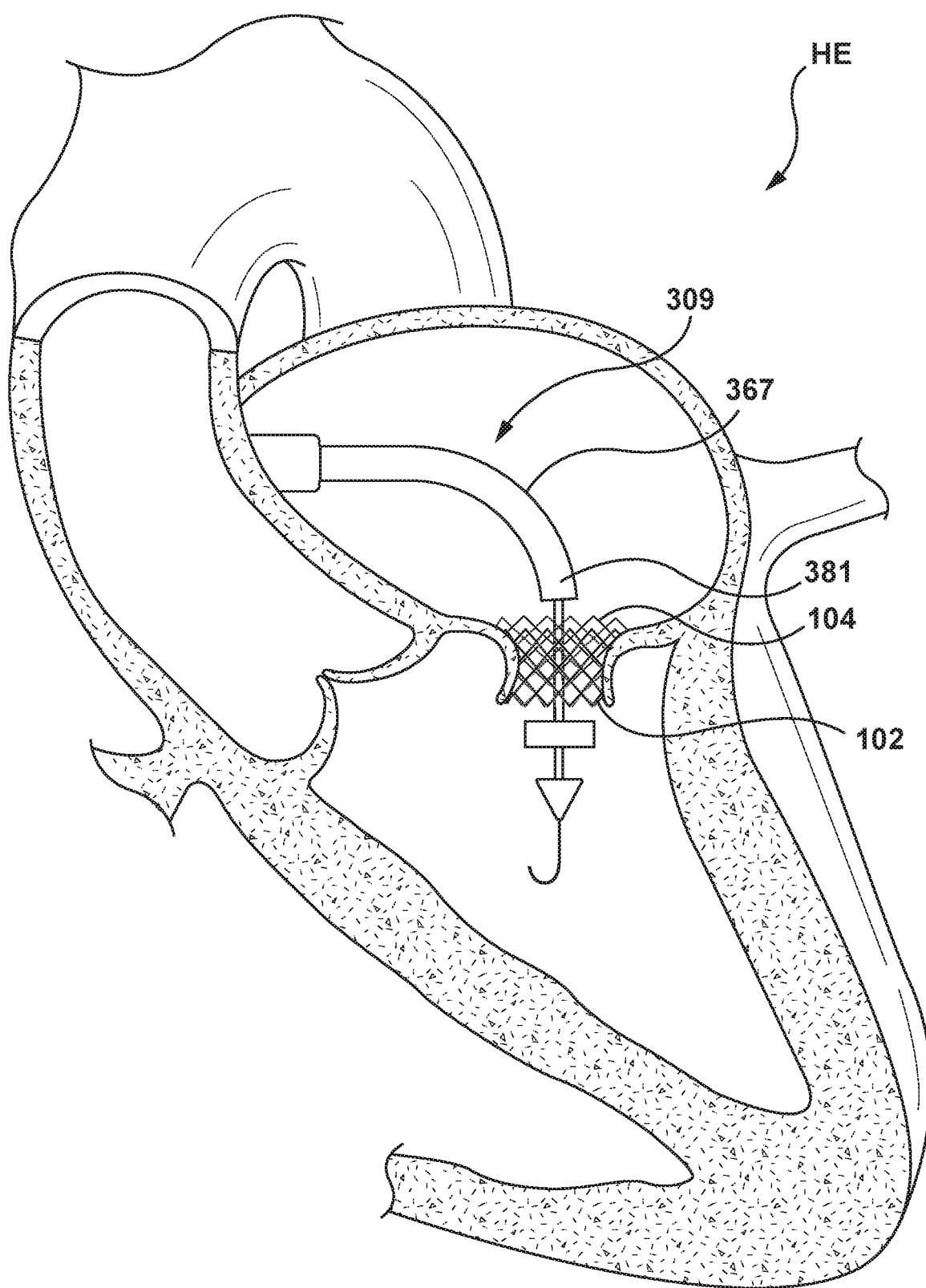
FIG. 16 is an illustration of the delivery system of FIG. 8 in situ, wherein the valve member has been released from the outer sheath of the valve sheath assembly, the valve member is in its radially expanded configuration within the docking member, and the orifice restriction mechanism is in its second state.

In a next step, with the valve member 104 positioned within the docking member 102, the handle 365 (not shown in FIGS. 10-16) of the valve sheath assembly 309 is manipulated to proximally retract the outer sheath 367 of the valve sheath assembly 309 to releasing the valve member 104 from the capsule 381 of the outer sheath 367. When released from the capsule 381, the valve member 104 expands radially to the radially expanded configuration such that the valve member 104 engages the deployed docking member 102, as shown in FIG. 16.

Following the successful positioning of the heart valve prosthesis 100, inflation fluid pressure is released and the orifice restriction mechanism 303 transitions from the second state to the first state. With the orifice restriction mechanism 303 in the first state, the valve sheath assembly 309 is distally advanced to receive the orifice restriction mechanism 303 in the first state within the lumen 389 of the inner sheath 369 of the valve sheath assembly 309. Thus, the inner sheath 369 of the valve sheath assembly 309 covers or encapsulates the orifice restriction mechanism 303 in the first state. Encapsulation of the orifice restriction mechanism 303 by the valve sheath assembly 309 assists in the atraumatic retraction and removal of the valve sheath assembly 309 and the inner shaft assembly 305 of the delivery system 301.

While the method of FIGS. 3-7 is described with the orifice restriction mechanism of FIGS. 2-2D and the method of FIGS. 10-16 is described with the orifice restriction mechanism of FIGS. 8A-8F, it will be understood by one of ordinary skill in the art that other embodiments of the orifice restriction mechanism may be utilized with a similar method, including, but not limited to the orifice restriction mechanism 403 of FIGS. 9A-9B or the orifice restriction mechanism 503 of FIGS. 9C-9D. In addition, although the methods of FIGS. 3-7 and FIGS. 10-16 each utilize the heart valve prosthesis 100 of FIG. 1, it will be understood by one of ordinary skill in the art that other embodiments of heart valve prostheses may be utilized with a similar method and that similar methods may be used at other locations.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for percutaneously delivering a heart valve prosthesis to a site of a native heart valve, the delivery system comprising:
   a delivery catheter including:
      an outer sheath;
      an inner shaft slidably disposed within the outer sheath; and
      an orifice restriction mechanism attached to a distal portion of the inner shaft, wherein the orifice restriction mechanism has a first state and a radially expanded second state, and wherein the orifice restriction mechanism moves with the inner shaft in both the first state and the radially expanded second state; and
   a heart valve prosthesis having a radially collapsed configuration and a radially expanded configuration, the heart valve prosthesis disposed within the outer sheath in the radially collapsed configuration in a delivery configuration of the delivery system,
   wherein the orifice restriction mechanism is configured to be positioned within the native heart valve and is configured to temporarily replicate the operation of the native heart valve until the heart valve prosthesis is deployed within the native heart valve.

2. The delivery system of claim 1, wherein the orifice restriction mechanism is configured to temporarily replicate the operation of the native heart valve by alternating between the first state and the radially expanded second state.

3. The delivery system of claim 1, wherein the heart valve prosthesis is a mitral heart valve prosthesis and the native heart valve is a native mitral valve.

4. The delivery system of claim 3, wherein the orifice restriction mechanism is configured to temporarily replicate the operation of the native valve by transitioning to the first state during diastole and transitioning to the radially expanded second state during systole of the cardiac cycle of a heart.

5. The delivery system of claim 1, wherein the orifice restriction mechanism comprises a balloon attached to the inner shaft.

6. The delivery system of claim 5, wherein:
the heart valve prosthesis comprises a docking member and a valve member;
the docking member is balloon expandable and is mounted on the balloon in the delivery configuration; and
the balloon is configured to radially expand the docking member and then temporarily replicate the operation of the native heart valve within the docking member until the valve member is deployed within the docking member.

7. The delivery system of claim 1, wherein the orifice restriction mechanism comprises a plurality of flaps attached to the inner shaft.

8. The delivery system of claim 7, wherein:
the heart valve prosthesis comprises a docking member and a heart valve member, the docking member is configured to be deployed at the site of the native heart valve; and
the orifice restriction member is configured to be disposed within the deployed docking member to replicate the operation of the native heart valve within the docking member until the valve member is deployed within the docking member.

9. A method of delivering, positioning and deploying a heart valve prosthesis at a site of a native heart valve, the method comprising the steps of:
advancing a delivery catheter with a heart valve prosthesis in a radially collapsed configuration retained therein and an orifice restriction member attached to the delivery catheter in a first state to the site of the native heart valve of a patient;
locating the orifice restriction member within the native heart valve;
cyclically alternating the orifice restriction mechanism between the first state and a radially expanded second state in synchronization with the cardiac cycle of the heart while the orifice restriction member is attached to the delivery catheter and located within the native heart valve;
deploying the heart valve prosthesis at the site of the native heart valve; and
removing the delivery catheter from the patient, thereby removing the orifice restriction member from the patient.

10. The method of claim 9, wherein the heart valve prosthesis includes a docking member and a valve member, wherein deploying the heart valve prosthesis comprises first deploying the docking member within the native heart valve and later deploying the valve member within the deployed docking member, wherein locating the orifice restriction member within the native heart valve comprises locating the orifice restriction member within the deployed docking member.

11. The method of claim 9, wherein the orifice restriction member comprises a balloon, and wherein cyclically alternating the orifice restriction member comprises inflating and deflating the balloon in synchronization with the cardiac cycle of the heart.

12. The method of claim 9, wherein the orifice restriction mechanism comprises a plurality of flaps attached to an inner shaft of the delivery catheter, wherein cyclically alternating the orifice restriction member comprises blood flow cyclically alternating the flaps between the first state and the second radially expandable state.

13. The method of claim 12, wherein each of the plurality of flaps comprises a first end pivotably coupled to the inner shaft and a second, free end opposite the first end, wherein the first state comprises the second end disposed adjacent the inner shaft, and the second radially expanded state comprises each flap pivotably rotating about the first end such that the second end is disposed radially outward of the first end such that a longitudinal axis of each flap is transverse to a central longitudinal axis of the inner shaft.

14. The method of claim 12, wherein locating the orifice restriction member comprises locating the orifice restriction member within a native mitral heart valve, and wherein the plurality of flaps pivot to the second radially expanded state during systole of the heart and to the first state during diastole of the heart.

15. The method of claim 9, wherein the orifice restriction mechanism is a radially expandable tube having a first end coupled to a distal end portion of a first inner shaft and a second end coupled to a distal end portion of a second inner shaft, wherein the second inner shaft is slidably received within a lumen of the first inner shaft, and wherein cyclically alternating the orifice restriction member comprises telescopically moving the first inner shaft relative to the second inner shaft.

16. The method of claim 15, wherein telescopically moving the first inner shaft relative to the second inner shaft such that the first end and the second end of the tube to move closer together causes the tube to radially expand and telescopically moving the first inner shaft relative to the second inner shaft such that the first end and the second end of the tube move farther apart causes the tube to radially collapse.

* * * * *